US011390971B2

(12) United States Patent
Nurkka

(10) Patent No.: US 11,390,971 B2
(45) Date of Patent: *Jul. 19, 2022

(54) SYSTEMS AND METHODS FOR MONITORING RESPIRATION IN A BIOSENSING GARMENT

(71) Applicant: Honeywell Safety Products USA, Inc., Fort Mill, SC (US)

(72) Inventor: Maria Elina Nurkka, Verdun (CA)

(73) Assignee: HONEYWELL SAFETY PRODUCTS USA, INC., Fort Mill, SC (US)

( * ) Notice: Subject to any disclaimer, the term of this patent is extended or adjusted under 35 U.S.C. 154(b) by 100 days.

This patent is subject to a terminal disclaimer.

(21) Appl. No.: 16/929,869

(22) Filed: Jul. 15, 2020

(65) Prior Publication Data

US 2020/0347531 A1 Nov. 5, 2020

Related U.S. Application Data

(63) Continuation of application No. 15/907,913, which is a continuation of application No. (Continued)

(51) Int. Cl.
*D04B 21/18* (2006.01)
*A61B 5/00* (2006.01)
(Continued)

(52) U.S. Cl.
CPC ............ *D04B 21/18* (2013.01); *A61B 5/0806* (2013.01); *A61B 5/6805* (2013.01); *G01B 7/16* (2013.01)

(58) Field of Classification Search
CPC .......... D04B 1/14; D04B 21/18; D04B 23/16; D04B 21/16; A61B 5/6802; A61B 5/6804; A61B 5/6806
(Continued)

(56) References Cited

U.S. PATENT DOCUMENTS 5,543,012 A 8/1996 Watson et al.
6,047,203 A 4/2000 Sackner et al.
(Continued)

FOREIGN PATENT DOCUMENTS

CN 1882280 A 12/2006
CN 101854856 A 10/2010
(Continued)

OTHER PUBLICATIONS

Chinese Office Action for Application No. 201680057590.9, dated Aug. 23, 2019 19 pages.
(Continued)

*Primary Examiner* — Danny Worrell
(74) *Attorney, Agent, or Firm* — Alston & Bird LLP

(57) ABSTRACT

Embodiments described herein relate generally to biosensing garments, and in particular, to systems and methods for monitoring respiration in a biosensing garment, whereby an improved integration of the respiration monitoring circuit into the garment is achieved, resulting in improved signal quality and durability. In some embodiments, an apparatus includes an elongate member having a longitudinal axis and configured to be stretchable along its longitudinal axis. The elongate member includes a plurality of elastic members (e.g., a first elastic member, a second elastic member, and a third elastic member) that extend along the longitudinal axis. A conductive member is coupled to the first, second and third members, and forms a "curved" pattern along the longitudinal axis of the elongate member. The conductive member is configured to change from a first configuration to a second configuration as the elongate member stretches along its longitudinal axis.

20 Claims, 33 Drawing Sheets

Related U.S. Application Data

PCT/CA2016/051034, filed on Aug. 31, 2016, now Pat. No. 10,753,021.

(60) Provisional application No. 62/247,049, filed on Oct. 27, 2015, provisional application No. 62/212,899, filed on Sep. 1, 2015.

(51) Int. Cl.
 *G01B 7/16* (2006.01)
 *A61B 5/08* (2006.01)

(58) Field of Classification Search
 USPC ..................................... 66/172 E, 202, 171
 See application file for complete search history.

(56) References Cited

U.S. PATENT DOCUMENTS

| | | |
|---|---|---|
| 6,341,504 B1 | 1/2002 | Istook |
| 6,551,252 B2 | 4/2003 | Sackner et al. |
| 7,559,902 B2 | 7/2009 | Ting et al. |
| 7,670,295 B2 | 3/2010 | Sackner et al. |
| 8,034,001 B2 | 10/2011 | Gal |
| 8,966,942 B2 | 3/2015 | Dias et al. |
| 2011/0087115 A1 | 4/2011 | Sackner et al. |
| 2014/0238151 A1 | 8/2014 | Dunne et al. |

FOREIGN PATENT DOCUMENTS

| | | |
|---|---|---|
| CN | 102138786 A | 8/2011 |
| CN | 202821331 U | 3/2013 |
| CN | 105007993 A | 10/2015 |

OTHER PUBLICATIONS

Final Rejection dated Jan. 10, 2020 for U.S. Appl. No. 15/907,913.
International Search Report and Written Opinion dated Nov. 25, 2016 for International Application No. PCT/CA2016/051034, 7 pages (OMSG-004/01WO).
Non-Final Rejection dated Oct. 1, 2019 for U.S. Appl. No. 15/907,913.
Notice of Allowance and Fees Due (PTOL-85) dated Apr. 15, 2020 for U.S. Appl. No. 15/907,913.
Office Action for Chinese Patent Application No. 201680057590.9 dated May 12, 2020, 18 pages.

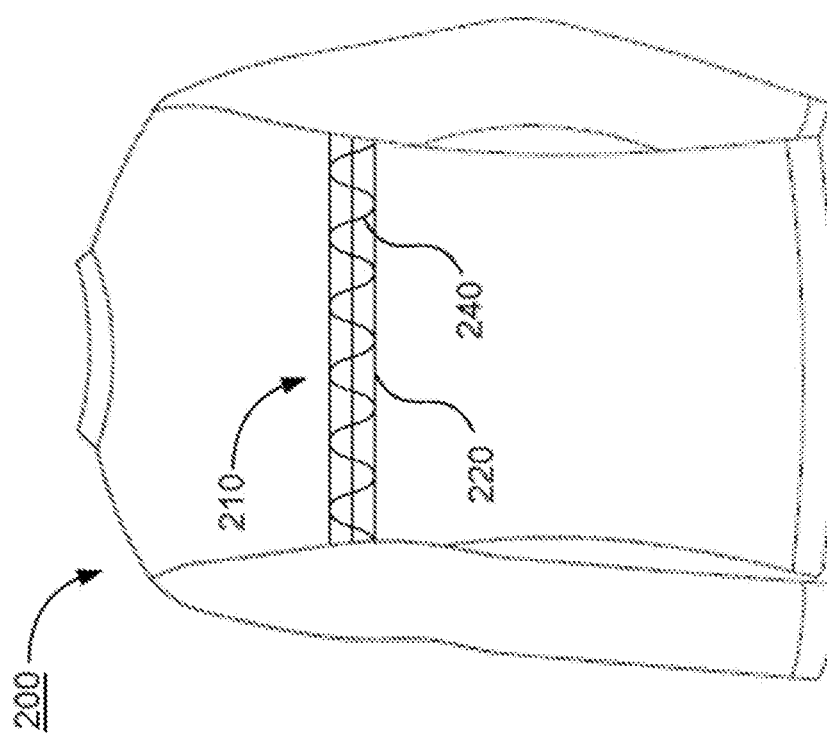
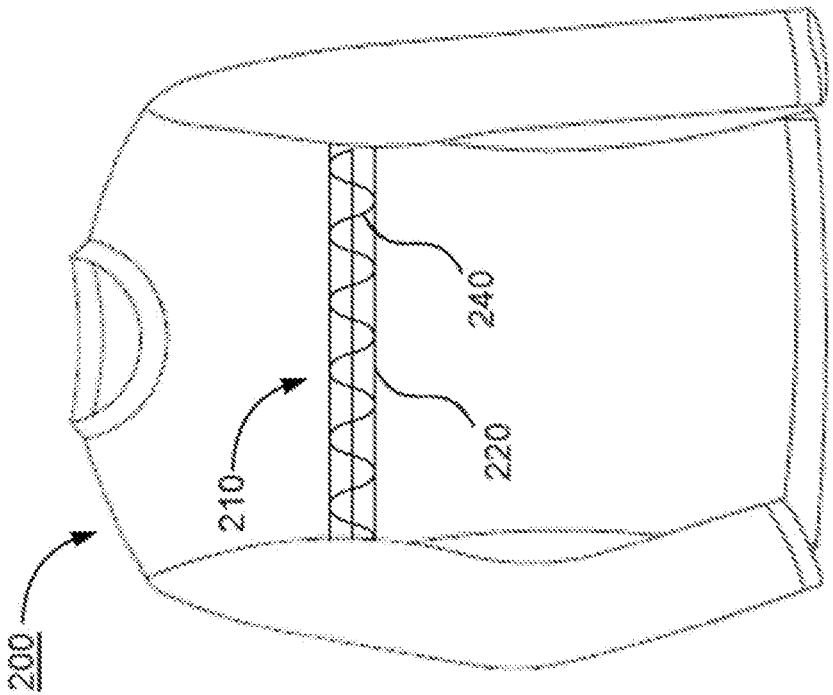

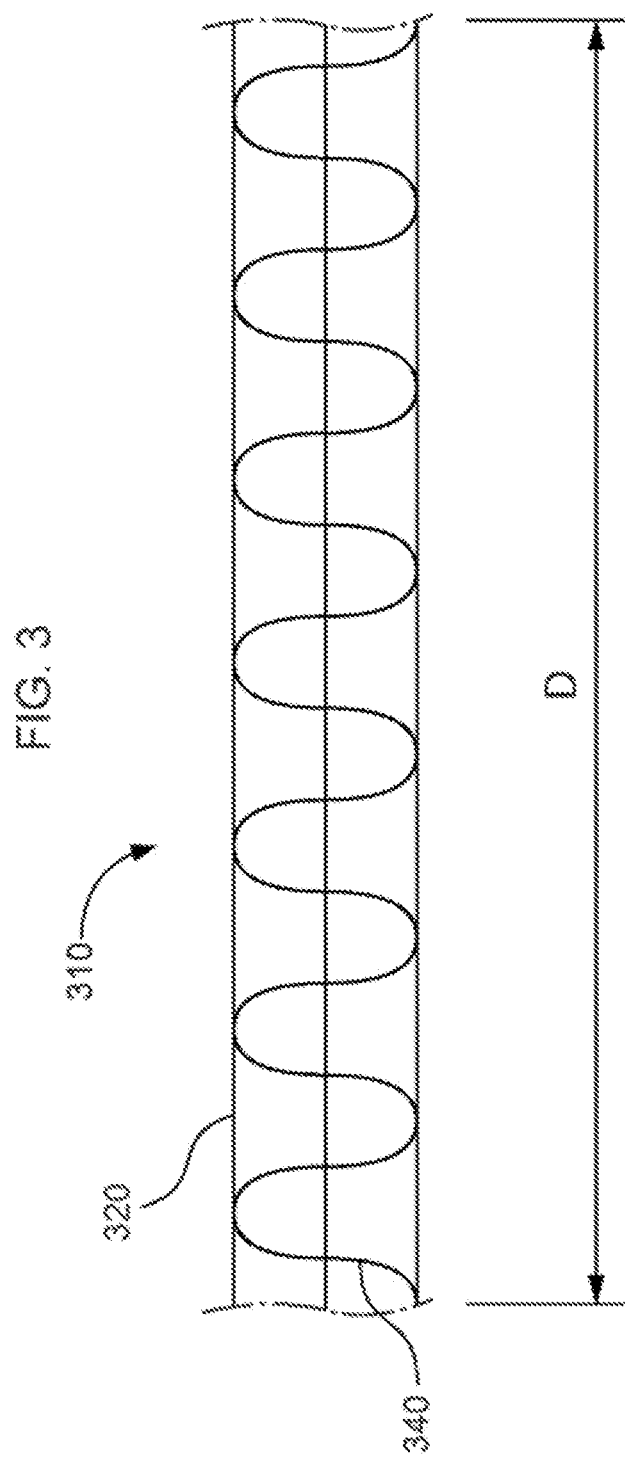

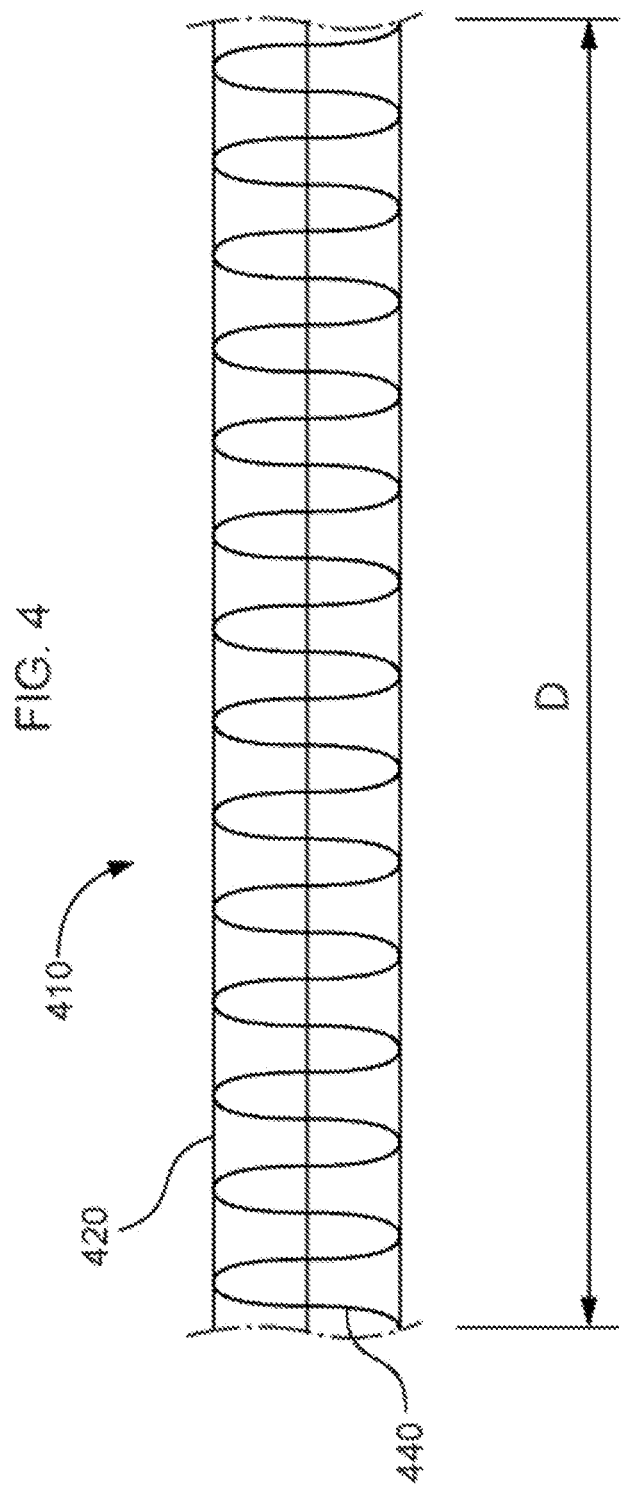

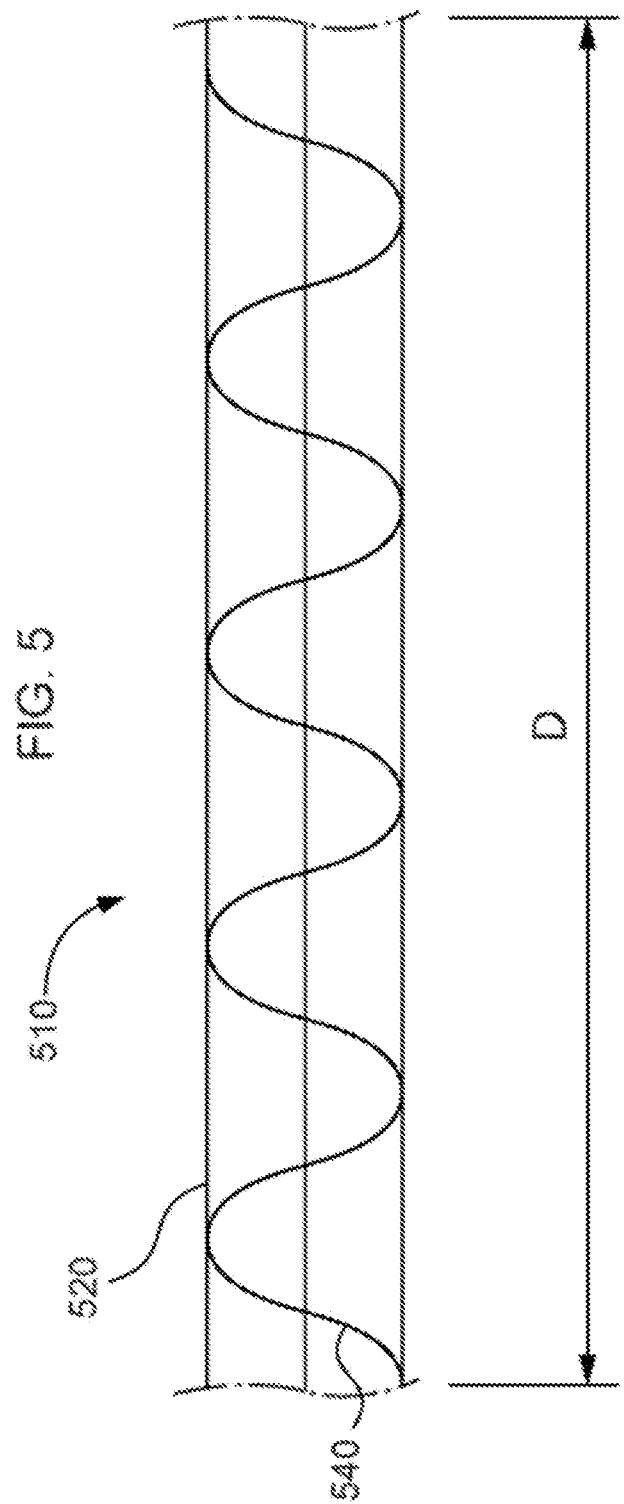

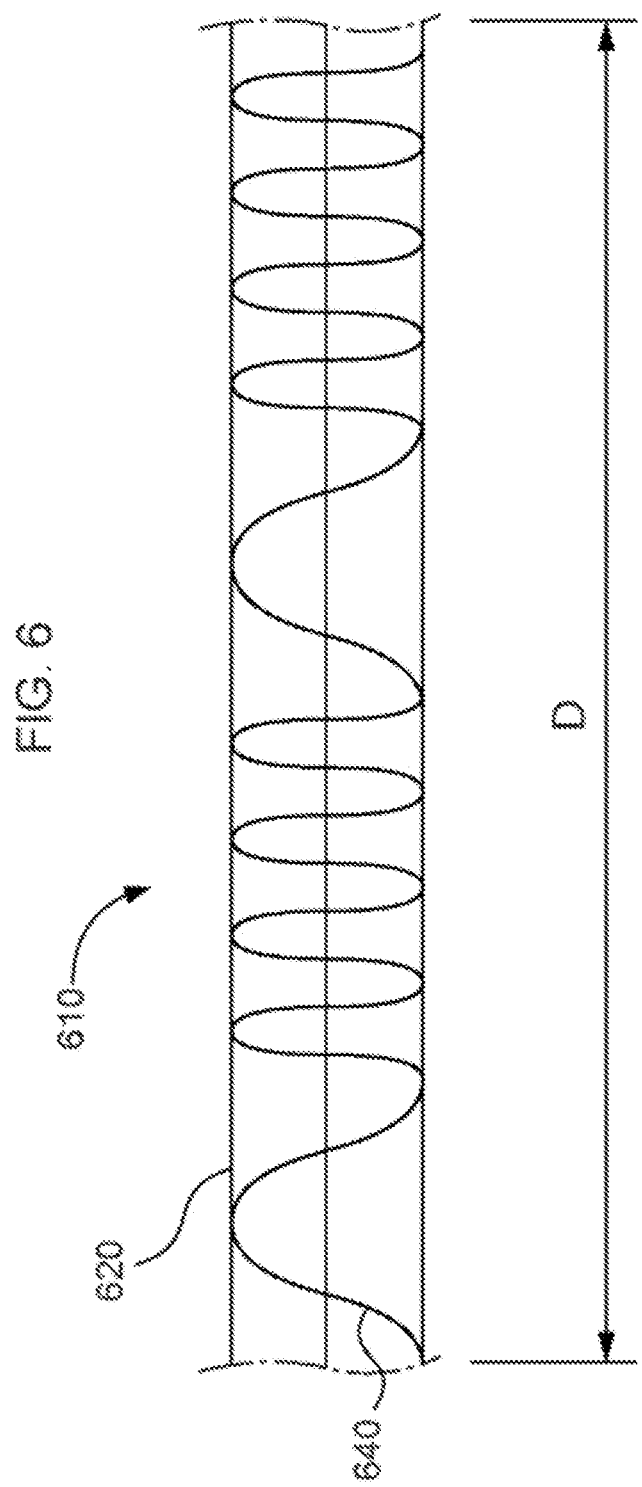

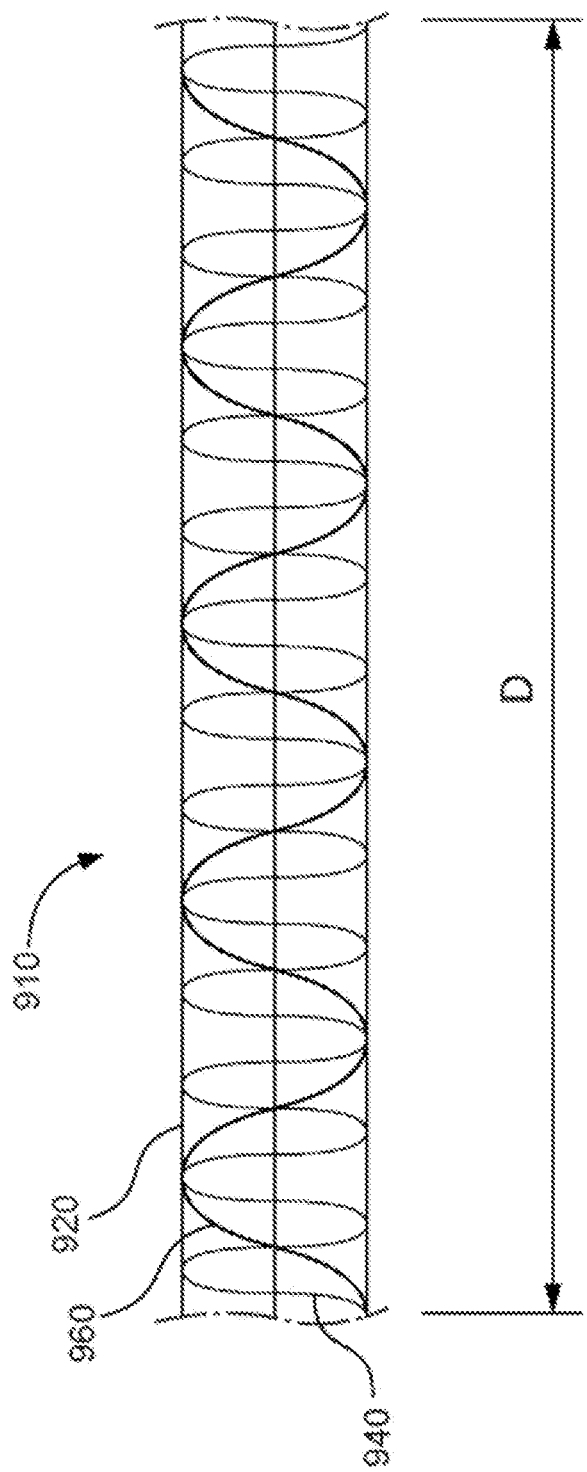

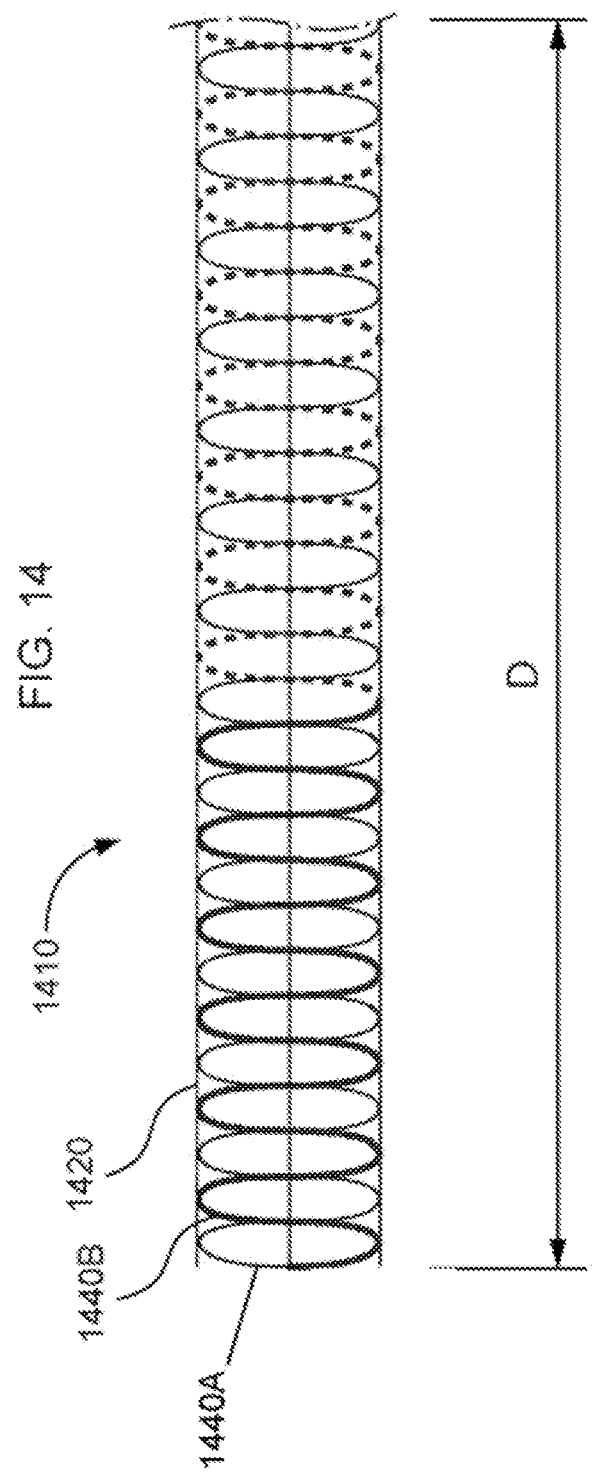

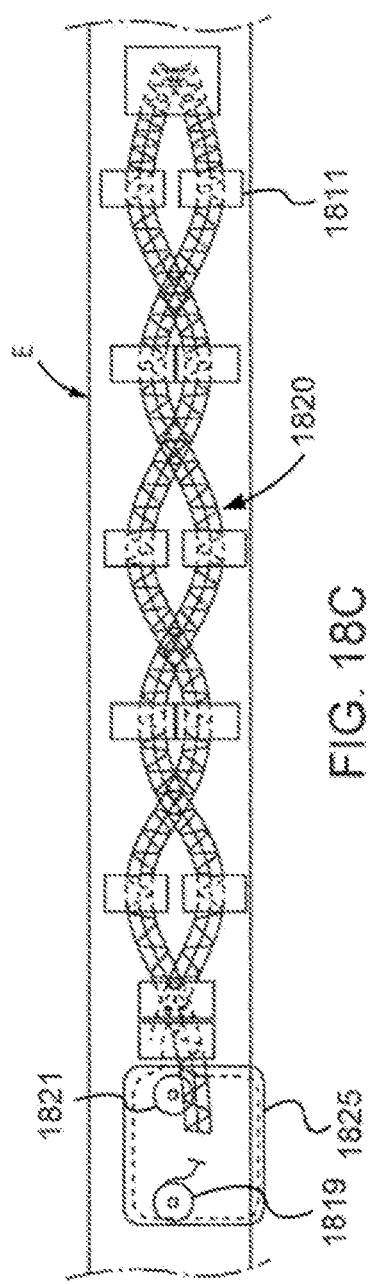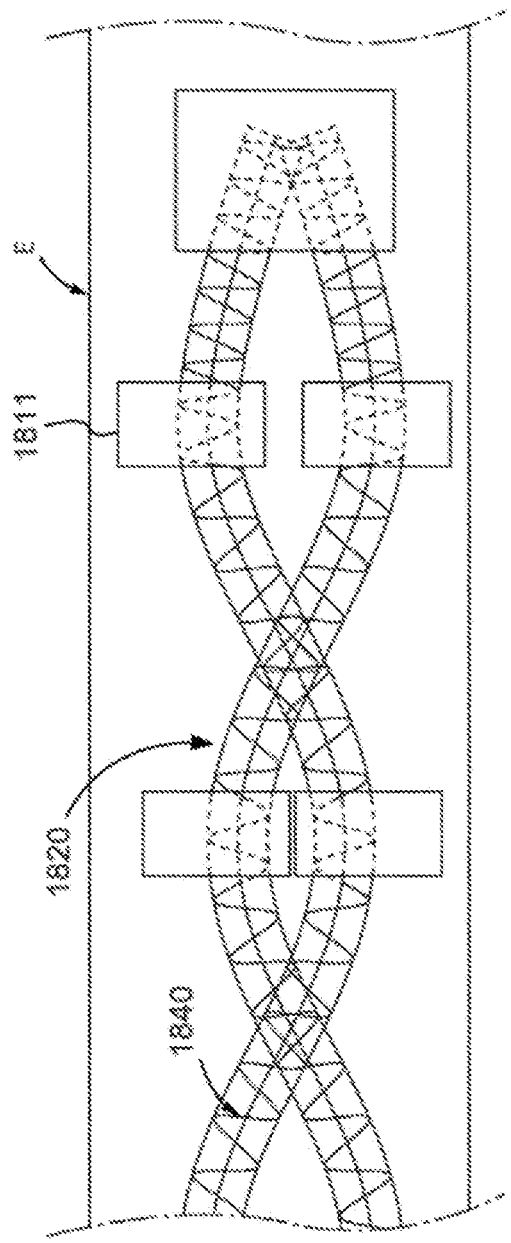

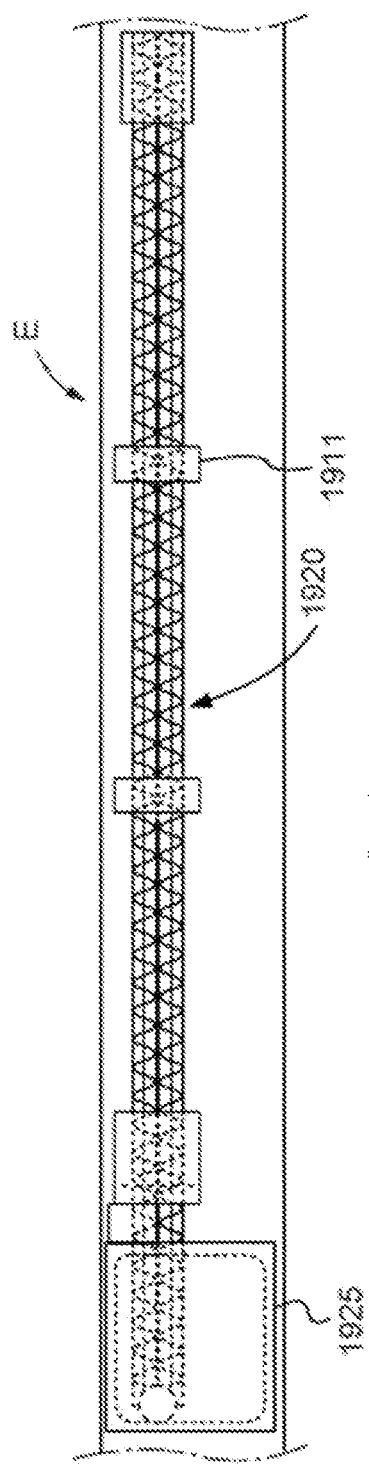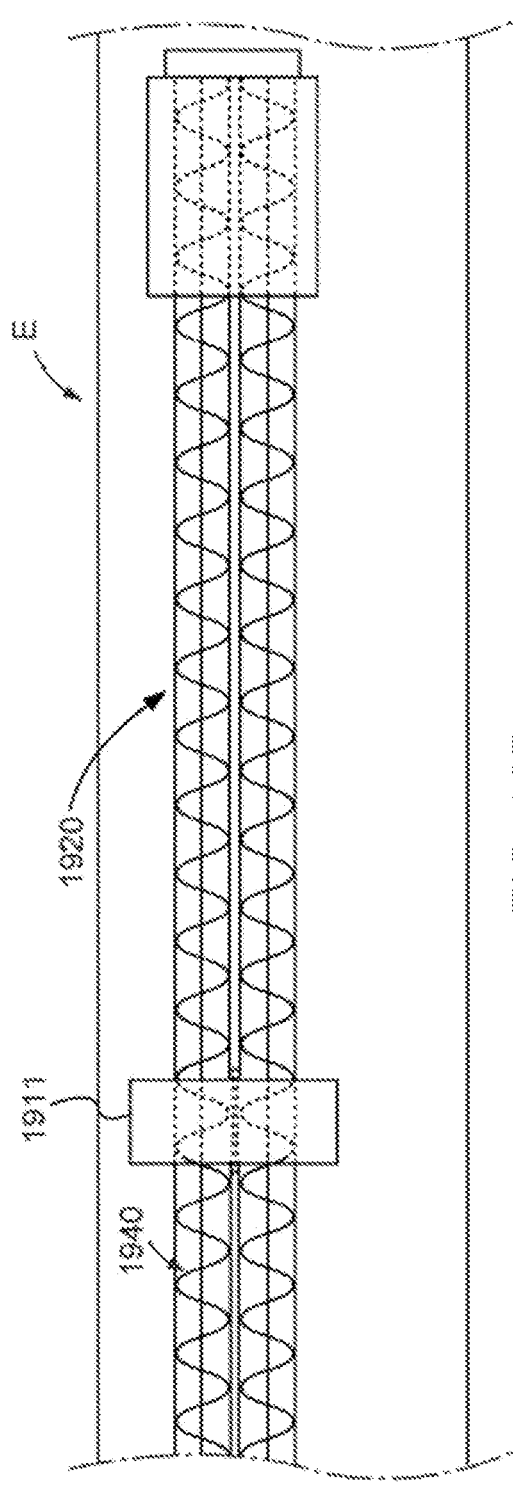

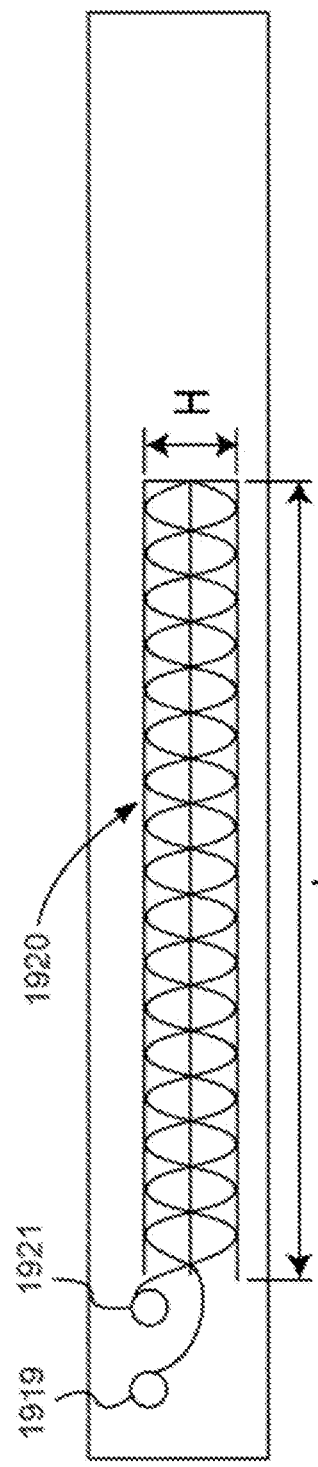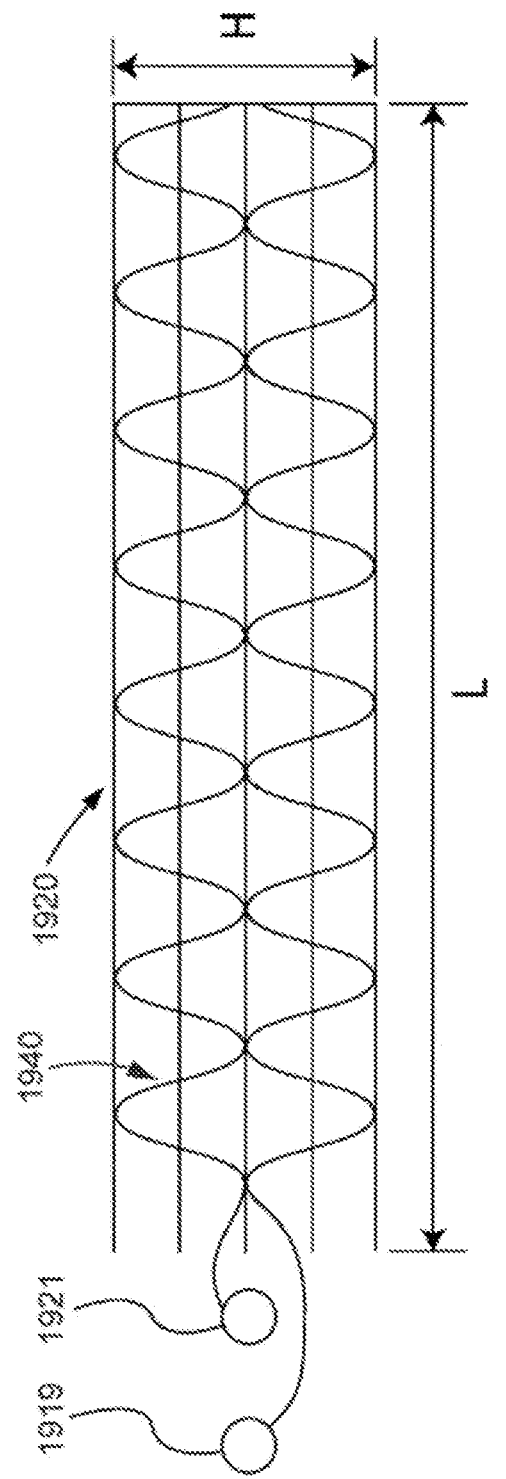

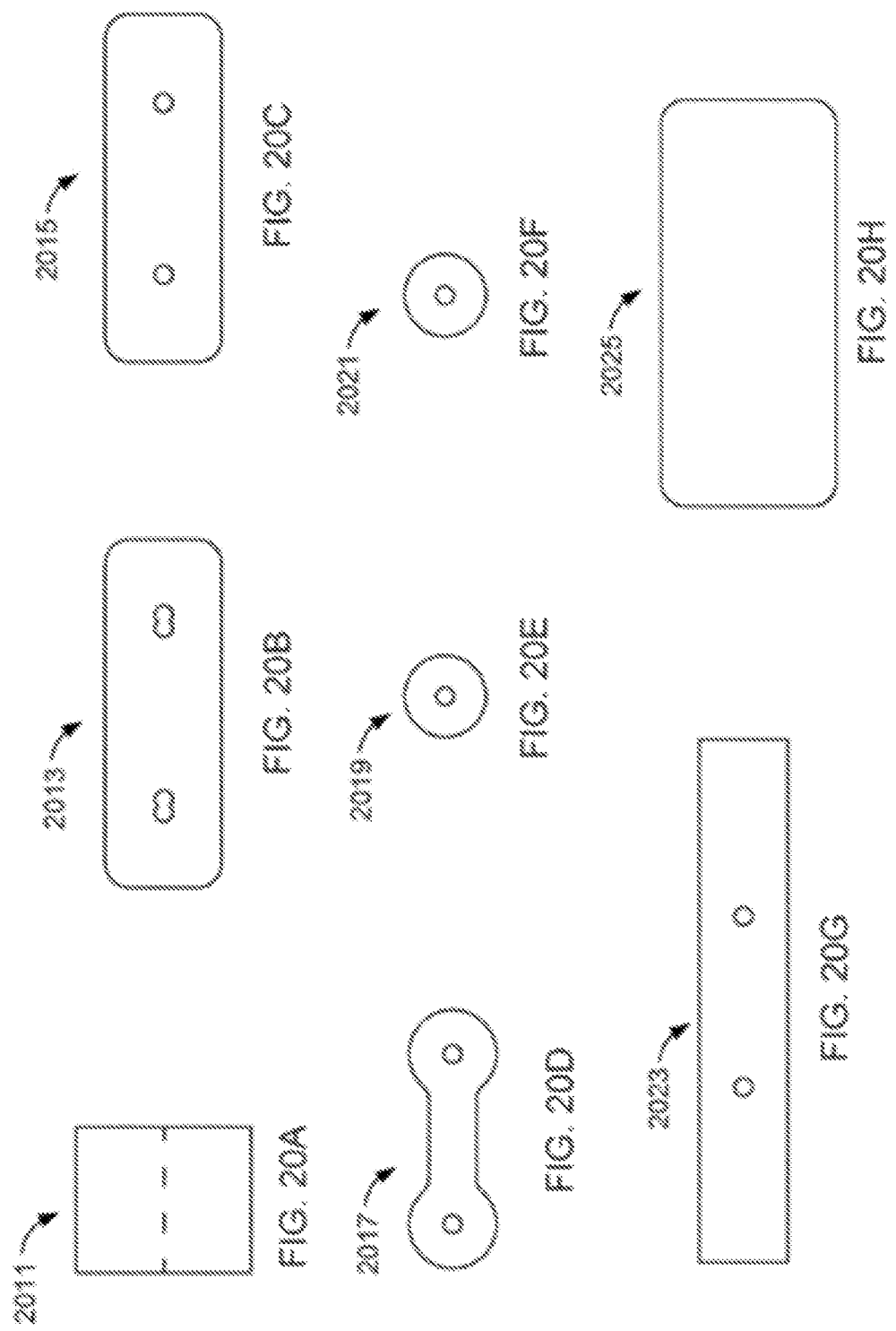

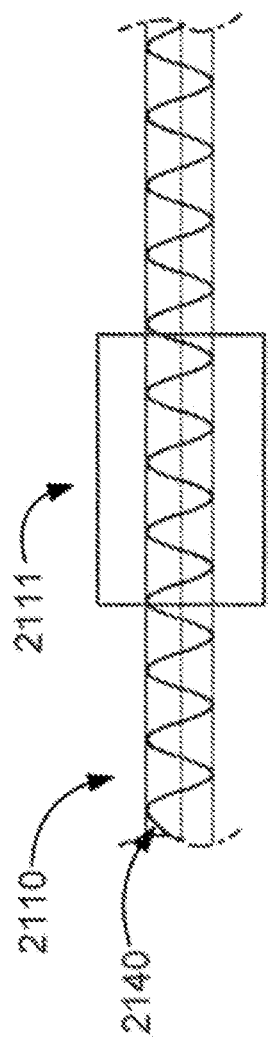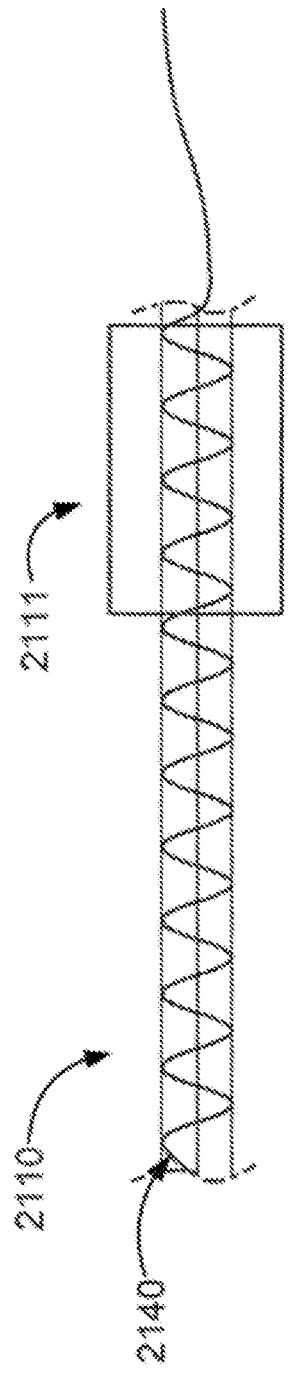

SYSTEMS AND METHODS FOR MONITORING RESPIRATION IN A BIOSENSING GARMENT

CROSS-REFERENCE TO RELATED APPLICATIONS

This application is a continuation of U.S. Non-Provisional patent application Ser. No. 15/907,913, filed Feb. 28, 2018, entitled "Systems and Methods for Monitoring Respiration in a Biosensing Garment," which is a continuation of International Patent Application Number PCT/CA2016/051034, filed Aug. 31, 2016, which claims priority to and the benefit of both U.S. Provisional Application No. 62/212,899, entitled "Systems And Methods For Monitoring Respiration In A Biosensing Garment," filed Sep. 1, 2015, and U.S. Provisional Application No. 62/247,049, entitled "Systems And Methods For Monitoring Respiration In A Biosensing Garment," filed Oct. 27, 2015, the entire disclosures of each of which are hereby incorporated herein by reference in their entireties for all purposes.

BACKGROUND

Consumers of wearable electronics and other electronic textiles ("e-textiles") demand ever-increasing levels of performance and functionality. Such functionality can include biosensors as well as interfaces with other smart technology. Although e-textile technology is theoretically applicable to a wide range of industries and applications, in practice electronic garment designs differ from traditional circuit designs in ways that make them less robust and, as a result, less reliable.

SUMMARY

Embodiments described herein relate generally to biosensing garments, and in particular, to systems and methods for monitoring respiration in a biosensing garment, whereby an improved integration of the respiration monitoring circuit into the garment is achieved, resulting in improved signal quality and durability. In some embodiments, an apparatus includes an elongate member having a longitudinal axis and configured to be stretchable along its longitudinal axis. The elongate member includes a plurality of elastic members (e.g., a first elastic member, a second elastic member, and a third elastic member) that extend along the longitudinal axis. For example, the elongate member can include a first elastic member extending along the longitudinal axis, a second elastic member that extends substantially parallel to the first elastic member, and a third elastic member that extends substantially parallel to the second elastic member. A conductive member is coupled to the first, second and third members, and forms a "curved" pattern along the longitudinal axis of the elongate member. The conductive member (and, correspondingly, its curved pattern) is configured to change from a first configuration to a second configuration as the elongate member stretches along its longitudinal axis. This change of configuration results in a change in an inductance value of the conductive member.

BRIEF DESCRIPTION OF THE DRAWINGS

FIG. 2A shows a front schematic plan view, and FIG. 2B shows a back schematic plan view, of a biosensing garment having an elongate member disposed on an interior surface thereof, according to an embodiment.

FIG. 3 is a schematic illustration of an elongate member, according to an embodiment.

FIG. 4 is a schematic illustration of an elongate member, according to an embodiment.

FIG. 5 is a schematic illustration of an elongate member, according to an embodiment.

FIG. 6 is a schematic illustration of an elongate member, according to an embodiment.

FIG. 9 is a schematic illustration of an elongate member, according to an embodiment.

FIG. 14 is a schematic illustration showing a folded configuration of an elongate member, according to some embodiments.

FIGS. 18C-18D are schematic illustrations showing a folded configuration of an elongate member incorporated into a garment, according to an embodiment.

FIGS. 19A-19B are schematic illustrations showing a folded configuration of an elongate member incorporated into a garment, according to an embodiment.

FIGS. 19C-19D are schematic illustrations showing a looped wire configuration of an elongate member incorporated into a garment, according to an embodiment.

FIGS. 20A-20H show components of an assembly process, according to an embodiment.

FIGS. 21A-21M show aspects of an assembly process, according to an embodiment.

DETAILED DESCRIPTION

Figure 1:
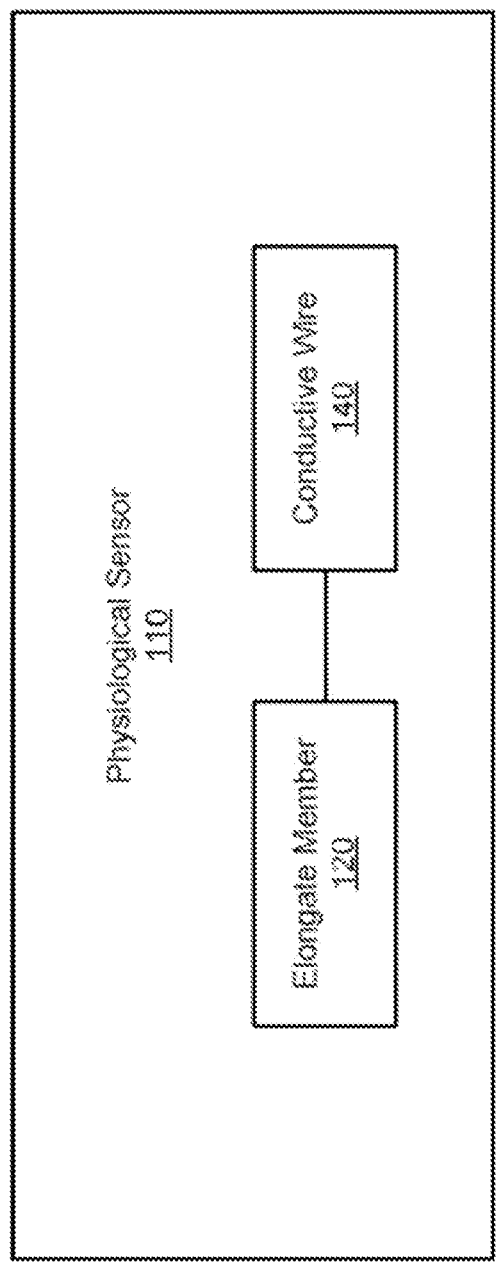
FIG. 1 is a schematic illustration of an elongate member according to an embodiment, in an exemplary environment.

Wearable electronics such as biosensing garments (and the electronic textiles from which they are made) are subjected to different mechanical stresses than traditional electronic systems. For example, biosensing garments may be stretched during enrobing, disrobing, and wear (e.g., during physical activity of the wearer). This stretching can result in deformation of conductors and/or sensor elements that are embedded within and/or secured to a surface of the biosensing garment. As a result, wearable electronics often suffer from compromised performance after only limited period of use. According to embodiments of the present disclosure, an improved integration of a physiological sensor (or components thereof) into a biosensing garment is achieved, resulting in improved signal quality, durability and reliability. Such physiological sensors include an elongate member and a conductive member (also referred to herein as a "conductive wire"). Specifically, embodiments of the present disclosure describe a respiration monitoring circuit that includes the elongate member and the conductive wire coupled to the elongate member in a pre-defined pattern and using knitting, braiding, weaving, and/or other attachment methods described herein.

Biosensing garments of the present disclosure are flexible enough to accommodate enrobing and disrobing ("putting on" and "taking off," respectively) in a manner that is comfortable or tolerable to a user, yet remains capable of detecting subtle changes in inductance during use, with an improved performance lifespan (e.g., reduced degradation of signal or "wearing out" of the biosensing infrastructure). In some embodiments, an elongate member, bearing an extensible, insulated or non-insulated (bare) conductive wire (collectively also referred to herein as a "breathing cable"), forms at least part of a respiration monitoring circuit (e.g., is a "respiratory inductance plethysmography" or "RIP" sensor), and is incorporated into a biosensing garment. The elongate member is configured to be disposed around an at least partial circumferential region of a wearer (also referred to herein as "user"). The at least partial circumferential region of the user may include at least a portion of the user's chest, rib cage, abdomen, and/or waist. The elongate member, when disposed about the circumference of a user, is configured to be held closely to the user's body. When the elongate member is disposed in this manner, the conductive wire has an intrinsic inductance value ("self-inductance") related to its shape or "pattern" (for example, its frequency, amplitude and/or periodicity). The inductance value of the conductive wire changes substantially proportionately in response to changes in the geometry (e.g., antero-posterior diameter, circumference, cross-sectional area, etc.) of the user's anatomy, for example as a result of the user's respiratory movements (breathing, inhalation, inspiration, exhalation, coughing, yawning, and/or the like) or other movements (exertion, muscle flexion, coughing, yawning, stretching, posture, and/or the like). The user's respiratory movements involve changes in the user's lung volume, compartmental torso volume, ventilation, inspired breath volume, etc. As a result, a user's lung volume, respiratory rate (e.g., breaths per minute), tidal volume, ventilation (e.g., minute ventilation), peak inspiratory flow, fractional inspiratory time, work of breathing, peak/mean inspiratory and expiratory flow, % RCi (percent contribution of rib cage excursions to the tidal volume), phase angle ("phi"), apnea status and/or classification, hypopnea status and/or classification, qDEEL (quantitative difference of end expiratory lung volume) and/or inspired breath volume, along with other parameters like breathing patterns, can be measured through transduction or "sensing" of the changing inductance (including the timing of such changes) of the conductive wire. In order to continuously measure the user's respiration, the conductive wire can be used as the inductor in a variable frequency LC oscillator (i.e., the conductive wire is connected to an LC circuit, in which the conductive wire acts as the inductor "L"). The LC oscillator can in turn be connected to a frequency-to-voltage converter, which can be connected to a scaling amplifier, which can be connected to a digital voltmeter or other suitable display.

Biosensing garments of the present disclosure include at least one, and in some embodiments multiple, elongate member/conductive wire combinations. Where multiple elongate member/conductive wire combinations are used, they may be co-located, or may be spaced apart by a pre-determined distance (for example, to measure and/or compare geometric information at disparate locations on a user's anatomy, e.g., substantially concurrently at the chest and the abdomen). In some embodiments, a biosensing garment comprises elastic fabric that is designed to fit over a user's body. At selected intervals, the elastic fabric includes one or more elongate members integrally (i.e., "monolithically") with it, and the elongate members can be impregnated with a conductive material, such as silver. The elongate members can be spaced, for example, in parallel pairs and can serve as electrodes for impedance plethysmography instruments to be attached. The elongate members themselves can be at least partially elastic. The conductive material can be aluminum, gold, copper, or any other suitable conductor material. Impregnated elongate members can be woven or knit into the elastic fabric at the selected intervals as the garment is being manufactured, such that the finished garment presents a uniform interior and/or exterior surface. For example, in some embodiments, the biosensing garment and/or sensors can be substantially similar to or the same as the biosensing garment, sensors and/or electrodes included in U.S. Patent Publication No. 2014/0343390 entitled, "Textile Blank With Seamless Knitted Electrode," ("the '390 Publication"), the disclosure of which is incorporated herein by reference in its entirety.

There are a number of drawbacks to existing biosensing garment technology. For example, in existing RIP sensor technology, differences in posture and/or thoraco-abdominal respiratory synchronization, accurate respiratory volumes often cannot be obtained using a single sensor (i.e., multiple sensors are required). Other difficulties include non-linear responses due to inexact coordination of the chest and abdomen (i.e., the two respiratory compartments). This makes certain respiratory indices difficult to measure, and limits the utility of some sensors to only respiration rates and other basic timing indices, and requiring a dual sensor system. Compounding these problems is the fact that existing RIP sensor implementations suffer from unwanted hysteresis effects, for example being unable to accommodate repeated use without changing its sensing characteristics. An illustration of the hysteresis-caused inductance variation of an RIP sensor "belt" that was stretched and released three times can be found in "A Wearable Respiration Monitoring System Based on Digital Respiratory Inductive Plethysmography," by Dan Wu, et al., Bulletin of Advanced Technology Research, Vol. 3, No. 9, September 2009. After an undesirably low amount of repeated use, not only do existing RIP sensors suffer from hysteretic effects (e.g., inelastically deformed, or "stretched out of shape"), but they can also become inoperable.

Embodiments of biosensing garment physiological sensors described herein provide several advantages over known biosensing garment sensors, such as: improved measurement-to-measurement signal consistency (i.e., high reproducibility), a more robust and prolonged sensor sensitivity (i.e., high reliability), ease and comfort of biosensing garment use, manufacturing efficiency, and reduced wear-related hysteresis.

FIG. 1 shows a schematic illustration of a physiological sensor 110 including an elongate member 120 and a conductive wire 140. The elongate member 120 is in contact with a conductive wire 140. The physiological sensor 110 can comprise an electronic textile, for example such that may be used in the manufacture of a biosensing garment. In some embodiments, the physiological sensor 110 comprises a biosensing garment (e.g., one or more of shirts, jerseys, vests, jackets, pants, shorts, bras, sports bras, bra camis, brassieres, swimsuits, hats, helmets, goggles, socks, shoes, footwear, headsets, watches, bracelets, underwear, athletic supporters, gloves, collars, neckbands, headbands, visors, scarves, mittens, arm sleeves, arm bands, leg sleeves, leg bands, head bands, waist bands, chest plates, tights, watches, undergarments, diapers, hospital gowns, bandages, smocks, girdles, blankets, and/or the like). The biosensing garment may comprise one or more textiles (e.g., cloths, fabrics etc.), for example consisting of a network of natural or artificial fibers. The textiles may derive from one or more sources, including plant sources (e.g., cotton, flax, hemp, jute, modal, bamboo, piria, ramie, milkweed stalk, lyocell, etc.), animal sources (e.g., wool, silk, milk proteins, etc.), mineral sources (e.g., glass fibers, etc.), and/or synthetic sources (e.g., nylon, polyester, polyamides, acrylic, aramid fibre, spandex, polyurethane, olefin fiber, ingeo, polylactide, lurex, carbon fibre, etc.). Strands from which the textiles are composed may include coatings such as waxes. Such textiles may be formed from one or more processes, including (but not limited to): weaving, knitting, crocheting, forming from tow, braiding, felting, thermal and/or mechanical bonding, and/or the like. As described herein, a textile formed by knitting is formed using any suitable knitting pattern or structure, for example, warp, weft, course/wale, knit-and-purl, plaited stitches, flat, circular, single, double, jersey, interlocked, mock rib, ribbed, two-way stretch, or any other suitable knitting pattern or combination thereof.

The elongate member 120 has a longitudinal axis and is stretchable along the longitudinal axis. The elongate member 120 includes a plurality of elastic members that can be arranged substantially in parallel with one another. In some embodiments, the elongate member 120 includes 2 elastic members. In some embodiments, the elongate member 120 includes 3 elastic members. In some embodiments, the elongate member 120 includes 3 elastic members. In some embodiments, the elongate member 120 includes up to 10 elastic members. In some embodiments, the elongate member 120 has a "width" (i.e., in a direction perpendicular to the longitudinal axis) of about 6 mm, or about 8 mm, or between about 6 mm and about 8 mm. At least one of the elastic members is knitted (using any suitable knitting method or structure as disclosed herein, for example: warp, weft, modified weft, weaving, course/wale, knit-and-purl, plaited stitches, flat, circular, single, double, jersey, interlocked, mock rib, ribbed, two-way stretch, or any other suitable knitting pattern or combination thereof) from a single yarn. The single yarn includes at least one elastic filament (e.g., elastane) and at least one non-elastic multifilament (e.g., nylon). In some embodiments, the elastic filament comprises one or more fibers, such as (but not limited to): nylon, modacrylic, olefin, polyolefins, acrylic, polyester, carbon fiber, rayon, vinyon, saran, spandex, vinalon, aramids (e.g., Nomax, Kevlar, or Twaron), modal, dyneema/spectra, polybenzimidazole fiber, sulfar, lyocell, polylactic acid (PLA), orlon, zylon, vectran, derclon, acrylonitrile rubber, glass fiber, metallic fiber, and polyhydroquinone-diimidazopyridine ("M5 fiber"), bamboo fiber, diacetate fiber, triacetate fiber, silicon carbide fibers, polymer fibers, polyamide nylon, polyethylene terephthalate ("PET") polyester or polybutylene terephthalate ("PBT") polyester, phenol-formaldehyde, elastane, elastolefin, and/or the like. In some embodiments, the non-elastic multifilament is texturized, for example to improve its stretchability. In some embodiments, the non-elastic multifilament comprises one or more fibers, such as (but not limited to): nylon, modacrylic, olefin, polyolefins, acrylic, polyester, carbon fiber, rayon, vinyon, saran, vinalon, aramids (e.g., Nomax, Kevlar, or Twaron), modal, dyneema/spectra, polybenzimidazole fiber, sulfar, lyocell, polylactic acid (PLA), orlon, zylon, vectran, derclon, acrylonitrile rubber, glass fiber, metallic fiber, and polyhydroquinone-diimidazopyridine ("M5 fiber"), bamboo fiber, diacetate fiber, triacetate fiber, silicon carbide fibers, polymer fibers, polyamide nylon, PET or PBT polyester, phenol-formaldehyde, and/or the like. In some embodiments, the yarn (or "thread") used in the knitting is a twisted yarn including 2 "strands" of multifilament nylon yarn and 1 filament of elastane that are twisted together. The composition of the yarn can be about 65% nylon and about 35% elastane. In some embodiments, each elastic member comprises a single yarn, and the single yarn comprises multiple filaments in a series of knitted loops. In some embodiments, the yarn comprises one or more texturized filaments, such as "curled" nylon.

In some embodiments, the yarn used to form one or more elastic members of the elongate member 120 comprises both elastane and a non-elastic or "conventional" fiber. In such embodiments, the combined elongate member and conductive wire exhibit certain desirable properties (for example due to the high "stretchability" of the yarn) that would not be observed if the same materials were used in isolation. For example, pure elastane fibers are relatively weak. When stretched into a tensile state, elastane fibers slowly begin to degrade, and they are easy to break once stretched beyond a maximum length. However, when combined with one or more non-elastic fibers, as described herein, the elastane is advantageously prevented from stretching to its maximum capacity (i.e., to the point of mechanical failure), and the structural integrity of the collective yarn is thus enhanced. Furthermore, the addition of elastane to the one or more non-elastic fibers enhances the mechanical stretchability of the collective yarn beyond what it would be if only non-elastic fibers were used.

The conductive wire 140 is any suitable electrical conductor (e.g., copper, aluminum, silver, tin, and/or alloys thereof, and/or any other conductive material, such as a metal, a metalloid, conductive paints or nanoparticle dispersions, a conductive polymer, a conductive ceramic material, etc.). For example, in some embodiments, the conductive wire 140 is 32 AWG silver plated copper wire (SPC), e.g., including 7 strands, that is insulated (e.g., with PVC, silicone, fluoropolymer resins such as PTFE, etc.). In some embodiments, the conductive wire 140 is a tinsel wire (silver plated copper alloy twisted around a textile yarn), a metal plated textile yarn that is insulated (e.g., with PTFE, silicone, etc.), or a "bare" metal plated textile yarn (i.e., that is not insulated). In some embodiments, using a bare metal plated textile yarn results in an improved signal strength and/or quality (e.g., in terms of amplitude, depth, noise). The conductive wire 140 can include multiple conductor "strands." For example, in some embodiments the conductive wire 140 includes 7 filaments. In some embodiments, the conductive wire 140 is coated with an electrically insulating layer (e.g., a plastics or rubberized material). In other words, the conductive wire 140 may be an insulated wire." For example, the conductive wire 140 may be a plastic-coated, silver-plated copper wire. In some embodiments, the conductive wire 140 is extensible or can be elastically deformed (e.g., by virtue of its physical configuration and/or the materials from which it is made).

The conductive wire 140 is in physical contact (i.e., "engaged") with each of the plurality of elastic members of the elongate member 120. In some embodiments, the conductive wire 140 is disposed on (e.g., atop, beneath, or adjacent to) one or more of the elastic members. In some embodiments, the conductive wire 140 is affixed to, knitted into (e.g., by weft knitting), woven into, interleaved with, enmeshed with, stitched to, looped through, braided with, or otherwise entangled with one or more of the elastic members. In some embodiments, the conductive wire 140 is affixed to, knitted into (e.g., by weft knitting), woven into, interleaved with, enmeshed with, stitched to, looped through, braided with, or otherwise entangled with one or more of the filaments of one of the elastic members. In some embodiments, the conductive wire 140 is affixed to, knitted into (e.g., by weft knitting), woven into, interleaved with, enmeshed with, stitched to, looped through, braided with, or otherwise entangled with one or more of the filaments of multiple elastic members. In some embodiments, the conductive wire 140, by way of its engagement with the elastic members, provides support to the elastic members (and, hence, to the elongate member 120). For example, the presence and positioning (e.g., attachment or coupling) of the conductive wire 140 with respect to the elastic members can help to set and/or maintain the spacing between two or more of the elastic members while also holding them together. In still further embodiments, the attachment between the conductive wire 140 and one or more elastic members (or portions thereof) can involve heat bonding with a fusible (hot melt) material (e.g., by a heat press or ironing). In such embodiments, one or more of the elastic members will have been knitted with fusible hot melt material, for example such that when multiple elastic members are assembled together (e.g., forming a "band" of elastic members), the fusible material is present on one side of the band of elastic members.

In some embodiments, a method of forming at least one of the plurality of elastic members of the elongate member 120 includes knitting individual yarns (for example, at multiple needles operating substantially "in parallel" or "serially" in time and/or physically "in parallel" or "serially") by producing a continuous series of loops. Separately or in parallel, the conductive wire 140 is "fed" through the elongate member 120, for example by passing the conductive wire 140 through at least one loop of at least one of the plurality of elastic members (i.e., that has been formed as herein described) such that it forms a predetermined pattern. By changing the wire "feed" per unit length (i.e., the length of conductive wire 140 per unit length of the elastic member and/or of the elongate member 120), different pattern shapes (e.g., periodicity, amplitude, and/or frequency) can be obtained. A "100% wire feed" is defined as the amount of conductive wire 140 per unit length (e.g., of the elongate member 120) that results in a straight wire profile (no oscillations). As such, exemplary wire feeds (or "feed rates") of the disclosure are 200% ((i.e., 2 times the length of wire required for a straight run for a given reference length, such that a meandering or sinusoidal pattern is established), 250% (i.e., 2.5 times the length of wire required for a straight run for a given reference length, such that a meandering or sinusoidal pattern is established) and 400% (i.e., 4 times the length of wire required for a straight run for a given reference length, such that a meandering or sinusoidal pattern is established). In some embodiments, using a higher feed rate or a higher frequency pattern (e.g., an increased number of sinusoidal oscillations per unit length, or a "higher periodicity") results in an improved signal strength and/or quality. In some embodiments, the "feed rate" (and, correspondingly, the frequency/amplitude of the resulting pattern) of the conductive wire 140 is selected such that when the stretchable physiological sensor 110 is elongated to its maximum, the conductive wire 140 still maintains a sinusoidal shape (i.e., the conductive wire 140 is not pulled straight). For values of the feed rate that are below the threshold value at which the conductive wire 140 is not flattened upon full elongation of the physiological sensor 110, increases in feed rate can have a significant effect on the robustness of the physiological sensor 110. In some embodiments, the conductive wire 140 is combined with the elastic members such that it has a curved (e.g., sinusoidal) pattern. In some embodiments, instead of a curved pattern, the conductive wire 140 is combined with the elastic members such that it has a sawtooth, square, or triangle shape along at least a portion of its length. In some embodiments, the elongate member 120 includes a single conductive wire 140 having a substantially constant pattern (i.e., shape and/or periodicity). In some embodiments, the elongate member 120 includes a single conductive wire 140 having a pattern (i.e., shape and/or periodicity) that varies along the longitudinal axis of the elongate member 120. Patterns of the conductive wires 140 described herein may be periodic, aperiodic, symmetric, and/or asymmetric along portions of or the entireties of their length(s).

In some embodiments, the patterns of the conductive wires 140 described herein may be present along only portions of the elongate member 120, with the rest of the elongate member 120 (and/or the conductive wire 140 embedded therewithin) being substantially "straight."

In some embodiments, a method of forming at least one of the plurality of elastic members of the elongate member 120 includes knitting individual yarns (for example, at multiple needles operating substantially "in parallel" or "serially" in time and/or physically "in parallel" or "serially") by producing a continuous series of loops. Multiple elastic members, each having thus been knitted into a continuous series of loops, are then knitted together to form the elongate member 120 (essentially, at this stage, an elongate knitted fabric). Separately or in parallel, the conductive wire 140 is "fed" through the elongate member 120, for example by passing the conductive wire 140 through at least one loop of at least one of the plurality of elongate members (i.e., that has been formed as herein described) such that it forms a predetermined pattern. For example, the conductive wire 140 may pass beneath one or more elastic member segments, then pass above one or more elastic member segments (e.g., portions of the interlocked loops or stitches of the knitting), continuing in an "over" and "under" manner in order to ensure a good integration of the conductive wire 140 into the elongate member 120. By changing the wire "feed" per unit length (i.e., the length of conductive wire 140 per unit length of the elastic member and/or of the elongate member 120), different pattern shapes (e.g., periodicity, amplitude, and/or frequency) can be obtained.

In some embodiments, multiple conductive wires 140 are coupled to the elongate member 120, the conductive wires 140 having substantially similar patterns (in terms of shape and/or periodicity). In some embodiments, multiple conductive wires 140 are coupled to the elongate member 120, each of said conductive wires 140 having a pattern (in terms of shape and/or periodicity) different from at least one of the other conductive wires. Where multiple conductive wires 140 are used, their patterns may be superimposed (e.g., one atop the other), or may be spatially arranged such that they run substantially parallel to one another along the longitudinal axis of the elongate member 120. In some embodiments, where multiple conductive wires 140 are used, those conductive wires 140 whose patterns are substantially similar may be arranged such that they are schematically "in phase" with one another (i.e., their peaks and valleys are aligned). In some embodiments, where multiple conductive wires 140 are used, conductive wires 140 whose patterns are substantially similar may be arranged such that they are schematically "out of phase" from one another (i.e., their peaks and valleys do not align, but rather are shifted along an axis with respect to one another). In some embodiments, using multiple conductive wires 140 results in an improved signal strength and/or quality (e.g., in terms of amplitude, depth, noise, and/or the like).

The elongate member 120 is disposed within and/or on a surface of the physiological sensor 110. For example, one or more portions of the elongate member 120 may be sewn, knitted (e.g., circular, "knitting in the round," single, double, jersey, interlocked, mock rib, ribbed, two-way stretch, or any other suitable knitting pattern or combination thereof), crocheted, felted, stitched, woven, or otherwise embedded into the physiological sensor. Instead or in addition, one or more portions of the elongate member 120 may be also glued, adhered, fastened, clipped, snapped, soldered, bonded, fused, or otherwise secured to a surface of the physiological sensor 110. The elongate member 120 can be positioned on or within the physiological sensor 110 in a number of configurations, as described in greater detail below. For example, the elongate member 120 can be disposed as a single, planar layer on a surface of the physiological sensor 110. In other embodiments, the elongate member 120 can follow a U-shaped path along a surface of the physiological sensor 110. In still other embodiments, the elongate member 120 can be disposed as a double layer that is folded back on itself (i.e., such that a single elongate member forms a two-ply layer along substantially the entirety of its length), on a surface of the physiological sensor 110. In some embodiments, the physiological sensor 110 is a biosensing garment, and the elongate member 120 (bearing the conductive wire 140) is attached to the shirt using one or more of the methods described herein. A portion of the insulating layer can be removed from both ends of the conductive wire 140, thereby exposing the bare conductor at each end. The exposed conductor can then be attached to a "connector" (e.g., a mechanical fastener that also provides for electrical connection), for example by placing it under a snap and laminating it in place to reinforce it. For embodiments in which the physiological sensor 110 comprises multiple conductive wires 140, portions of the insulating layer can be removed from both ends of each of the multiple conductive wires 140 and attached to a common connector. In such embodiments, the electrical resistance of the physiological sensor 110 is proportionally reduced (e.g., approximately halved, in the case of two wires), thereby improving the signal quality and reducing power consumption. In some embodiments, the elongate member 120 is formed integrally or "monolithically" with the physiological sensor 110. The physiological sensor 110 may include one or more electrical leads connectable with a unit for receiving data from the physiological sensor 110 and for storing the data in a computer-readable medium. The unit may be configured to communicate (e.g., wirelessly) with a central data repository for receiving, storing and processing data generated by the physiological sensor 110, and for making stored data available to the user and/or to others (e.g., a health care provider).

FIG. 2A shows a front schematic plan view, and FIG. 2B shows a back schematic plan view, of a biosensing garment 200 incorporating a physiological sensor 210 as described herein. Although the biosensing garment 200 in FIGS. 2A and 2B is shown as a biosensing shirt, embodiments of biosensing garments as described herein can be any type of garment (e.g., one or more of shirts, jerseys, vests, jackets, pants, shorts, bras, sports bras, bra camis, brassieres, swimsuits, hats, helmets, goggles, socks, shoes, footwear, headsets, watches, bracelets, underwear, athletic supporters, gloves, collars, neckbands, headbands, visors, scarves, mittens, arm sleeves, arm bands, leg sleeves, leg bands, head bands, waist bands, chest plates, tights, watches, undergarments, diapers, hospital gowns, bandages, smocks, girdles, blankets, and/or the like).

In some embodiments, the physiological sensor 210 includes an elongate member 220 and a conductive wire 240 having a substantially sinusoidal pattern coupled to the elongate member 220 to form at least part of the respiration monitoring sensor 210 (e.g., a "respiratory inductance plethysmography" or "RIP" sensor). In some embodiments, the physiological sensor 210 is disposed on an interior surface of the biosensing garment 200. The elongate member 220 is configured to be disposed around an at least partial circumferential region of a user. The at least partial circumferential region of the user can include at least a portion of the user's chest, rib cage and/or abdomen. The elongate member 220, when disposed about the circumference of a user as shown in FIGS. 2A and 2B, is configured to be held closely to the user's body. The conductive wire 240 has an intrinsic inductance value ("self-inductance") related to its sinusoidal shape or "pattern" (for example, related to a frequency, amplitude and/or periodicity thereof). The inductance value of the conductive wire 240 changes substantially proportionately in response to changes in the geometry (e.g., antero-posterior diameter, circumference, cross-sectional area, etc.) of the user's anatomy, for example as a result of the user's respiratory movements (breathing, inhalation, inspiration, exhalation, coughing, yawning, and/or the like) or other movements (exertion, muscle flexion, coughing, yawning, stretching, posture, and/or the like). The user's respiratory movements involve changes in the user's lung volume, compartmental torso volume, ventilation, inspired breath volume, etc. As a result, a user's lung volume, respiratory rate (e.g., breaths per minute), tidal volume, ventilation (e.g., minute ventilation), peak inspiratory flow, fractional inspiratory time, work of breathing, peak/mean inspiratory and expiratory flow, % RCi (percent contribution of rib cage excursions to the tidal volume), phase angle ("phi"), apnea status and/or classification, hypopnea status and/or classification, qDEEL (quantitative difference of end expiratory lung volume) and/or inspired breath volume, along with other parameters like breathing patterns, can be measured through transduction or "sensing" of the changing inductance (including the timing of such changes) of the conductive wire. In order to continuously measure the user's respiration, the conductive wire can be used as the inductor in a variable frequency LC oscillator (i.e., the conductive wire is connected to an LC circuit, in which the conductive wire acts as the inductor "L"). The LC oscillator can in turn be connected to a frequency-to-voltage converter, which can be connected to a scaling amplifier, which can be connected to a digital voltmeter or other suitable display. In some embodiments, the physiological sensor 210 is incorporated into the biosensing garment 200 during the manufacturing of the biosensing garment 200. In some embodiments, the elongate members 220 and the conductive wire 240 are knitted on sequential tubular textile sections that are connected to further tubular textile sections, followed by folding over and stitching together the necessary components in order to assemble the biosensing garment 200. In still further embodiments, the elongate members 220 and the conductive wire 240 are knitted into a tubular "band" independent of the manufacturing of the biosensing garment 200. In such embodiments, the tubular band is printed and/or laminated with insulation while not yet incorporated into the biosensing garment 200, and then the tubular band is integrated into a completed biosensing garment 200 through stitching and/or bonding.

FIG. 3 is a schematic illustration of an elongate member 320 for incorporation into and/or use as a physiological sensor 310, according to an embodiment. A conductive wire 340 having a continuous substantially sinusoidal pattern is coupled to the elongate member 320. The elongate member 320 can be of any length suitable for a physiological sensing application (e.g., of sufficient length to cover the at least partial circumferential region of a user discussed above). The pattern of the conductive wire 340 may be said to have a periodicity of about 7 over a distance "D."

FIG. 4 is a schematic illustration of an elongate member 420 for incorporation into and/or use as a physiological sensor 410, according to an embodiment. A conductive wire 440 having a continuous substantially sinusoidal pattern is coupled to the elongate member 420. The elongate member 420 can be of any length suitable for a physiological sensing application (e.g., of sufficient length to cover the at least partial circumferential region of a user discussed above). The pattern of the conductive wire 440 may be said to have a periodicity of about 14 over distance D.

FIG. 5 is a schematic illustration of an elongate member 520 for incorporation into and/or use as a physiological sensor 510, according to an embodiment. A conductive wire 540 having a continuous substantially sinusoidal pattern is coupled to the elongate member 520. The elongate member 520 can be of any length suitable for a physiological sensing application (e.g., of sufficient length to cover the at least partial circumferential region of a user discussed above). The pattern of the conductive wire 540 may be said to have a periodicity of about 4.5 over distance D.

FIG. 6 is a schematic illustration of an elongate member 620 for incorporation into and/or use as a physiological sensor 610, according to an embodiment. A conductive wire 640 having a continuous, asymmetric pattern of varying periodicity is coupled to the elongate member 620. The elongate member 620 can be of any length suitable for a physiological sensing application (e.g., of sufficient length to cover the at least partial circumferential region of a user discussed above). The pattern of the conductive wire 640 may be said to include regions having a periodicity of about 1, and regions having a periodicity of about 4. Said regions having a periodicity of about 1, and regions having a periodicity of about 4 may be said to "alternate" along a longitudinal axis of the elongate member 620. A single region having a periodicity of about 1 and a single region having a periodicity of about 4, when viewed together, may be said to collectively comprise a "composite pattern," said composite pattern having a periodicity of 2 over distance D.

Figure 7A:
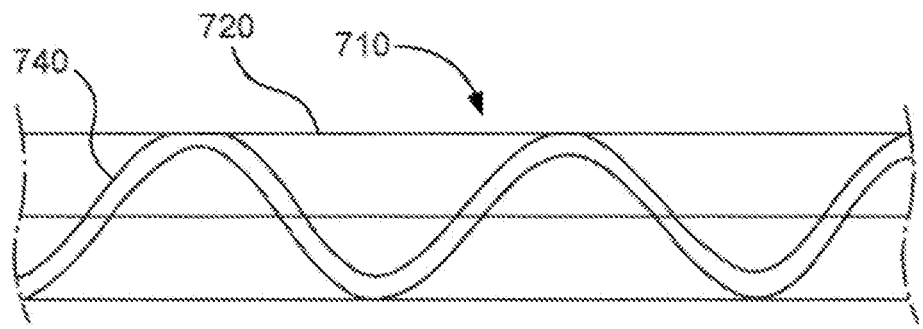
FIGS. 7A-7C are schematic illustrations showing elongate member/conductive wire combinations, according to embodiments of the disclosure.
Figure 7B:
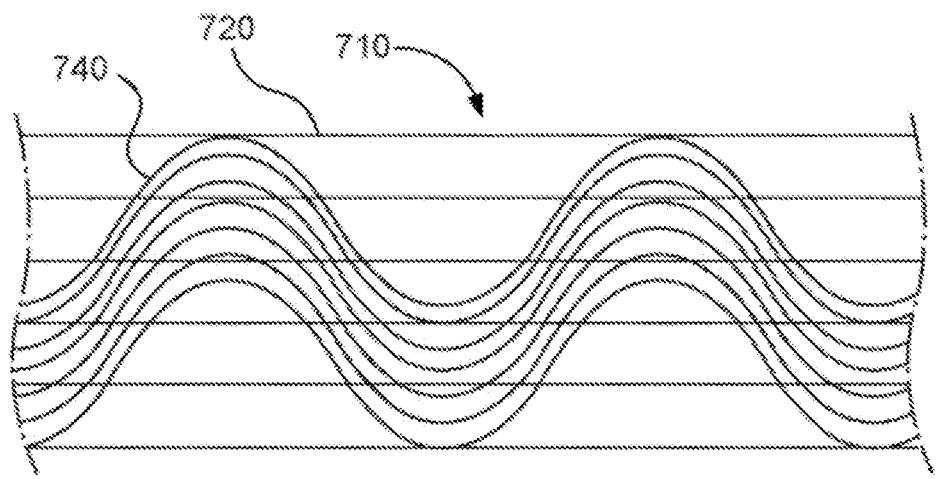
Figure 7C:
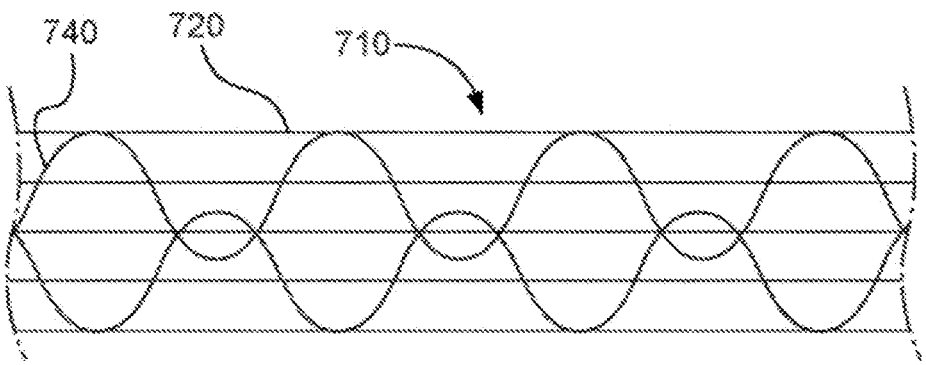

FIGS. 7A-7C show schematic illustrations of elongate member/conductive wire combinations (also referred to herein as "constructions," or "tape") for incorporation into and/or use as a physiological sensor 710, including an elongate member 720 and a plurality of conductive wires 740, according to embodiments of the disclosure. FIGS. 7A and 7B depict elongate member/conductive wire combinations (having two and seven periodic conducting wires, respectively) that have been knitted with a fusing thread and are loosely connected to one side of the tape. FIG. 7C shows an elongate member/conductive wire combination, having two periodic conductive wires that are substantially out-of-phase with one another and partially overlapping, that has been found to show superior signal detection and accuracy.

Figure 8A:
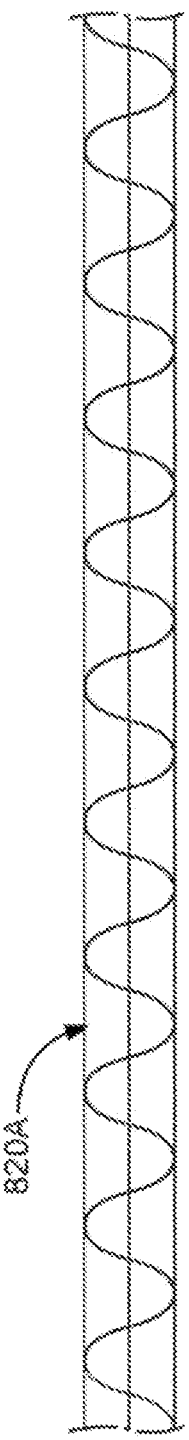
FIGS. 8A and 8B show elongate members, according to embodiments of the disclosure.
Figure 8B:
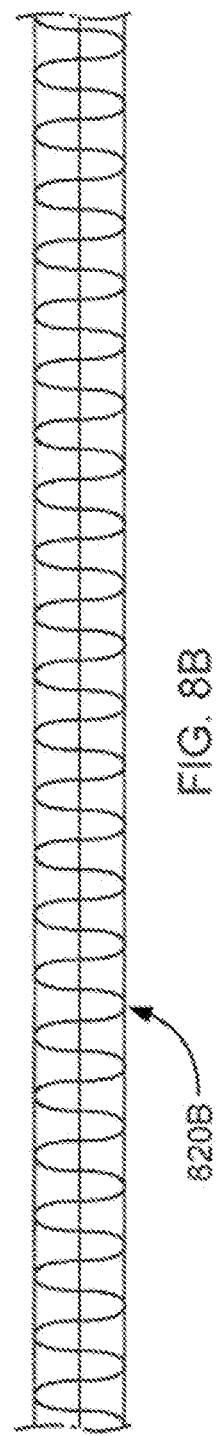

FIG. 8A shows a first elongate member (or "tape") 820A, and FIG. 8B shows a second elongate member (or "tape") 820B, both in a "relaxed" (i.e., not stretched) configuration, according to embodiments of the disclosure. Elongate members 820A and 820B have wire feeds of about 200% and about 400%, respectively. The frequency of the first elongate member 820A is about half the frequency of the second elongate member 820B. In other words, the period of the first elongate member 820A is about double the period of the second elongate member 820B. The second elongate member 820B may be said to comprise a "denser" sinusoid than the first elongate member 820A. In some embodiments, the elongate members 820A and 820B are approximately 8 mm wide.

FIG. 9 is a schematic illustration of an elongate member 920, for incorporation into and/or use as a physiological sensor 910, according to an embodiment. A first conductive wire 940, having a continuous substantially sinusoidal pattern, is coupled to the elongate member 920. The pattern of the conductive wire 940 may be said to have a periodicity of about 14 over distance D. A second conductive wire 960, having a continuous substantially sinusoidal pattern, is also coupled to the elongate member 920. The pattern of the conductive wire 960 may be said to have a periodicity of about 4.5 over distance D. As such, the frequency of the first conductive wire 940 has about three times the frequency of the second conductive wire 960. In other words, the period of the first conductive wire 940 is about one-third the period of the second conductive wire 960.

Figure 10A:
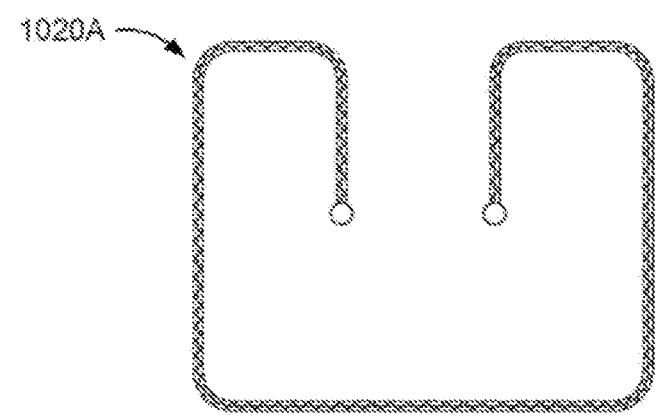
FIGS. 10A-10C are schematic illustrations showing configurations of an elongate member, according to some embodiments.
Figure 10B:
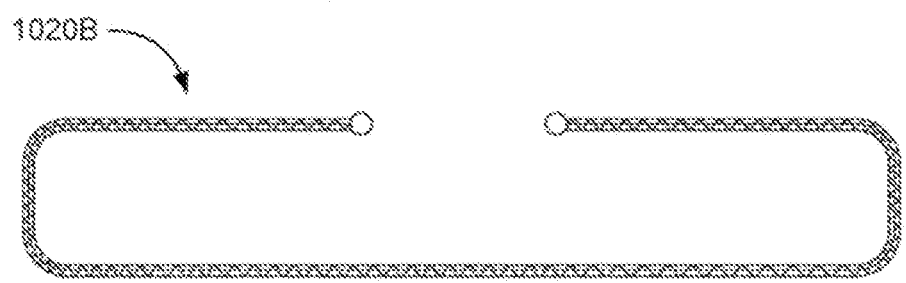
Figure 10C:

FIGS. 10A-C show three example (open loop) configurations of elongate members with conductive wires coupled thereto, according to some embodiments: FIG. 10A illustrates a substantially square or "u-shaped" configuration 1020A; FIG. 10B illustrates a substantially rectangular-shaped configuration 1020B; and FIG. 10C illustrates a substantially circular shape/configuration 1020C. In some embodiments, the configurations of elongate members include at least one of a substantially oval shape, and any other shape, including an irregularly shape.

Figure 11:
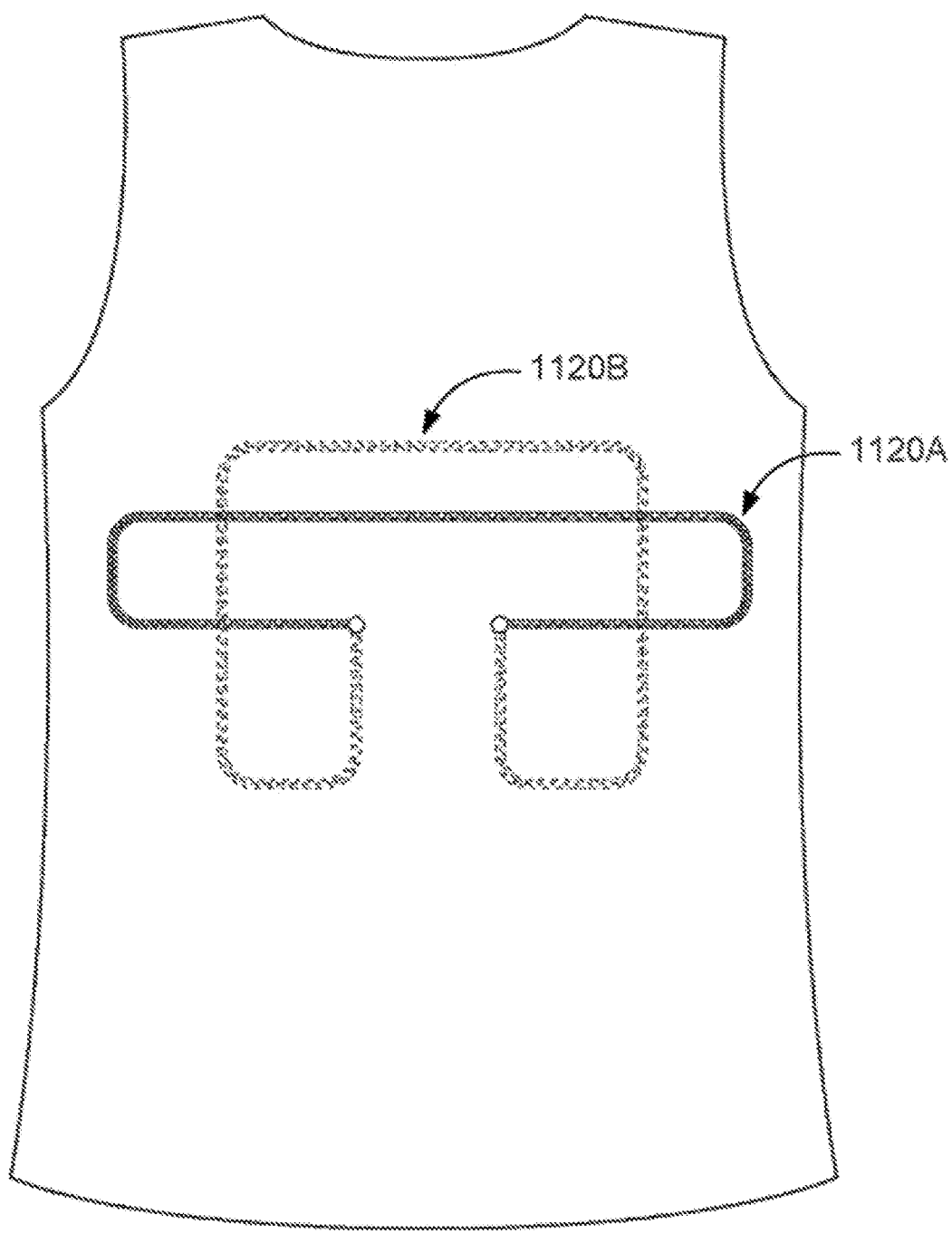
FIG. 11 is a schematic illustration showing a configuration of an elongate member, according to some embodiments.
Figure 12:
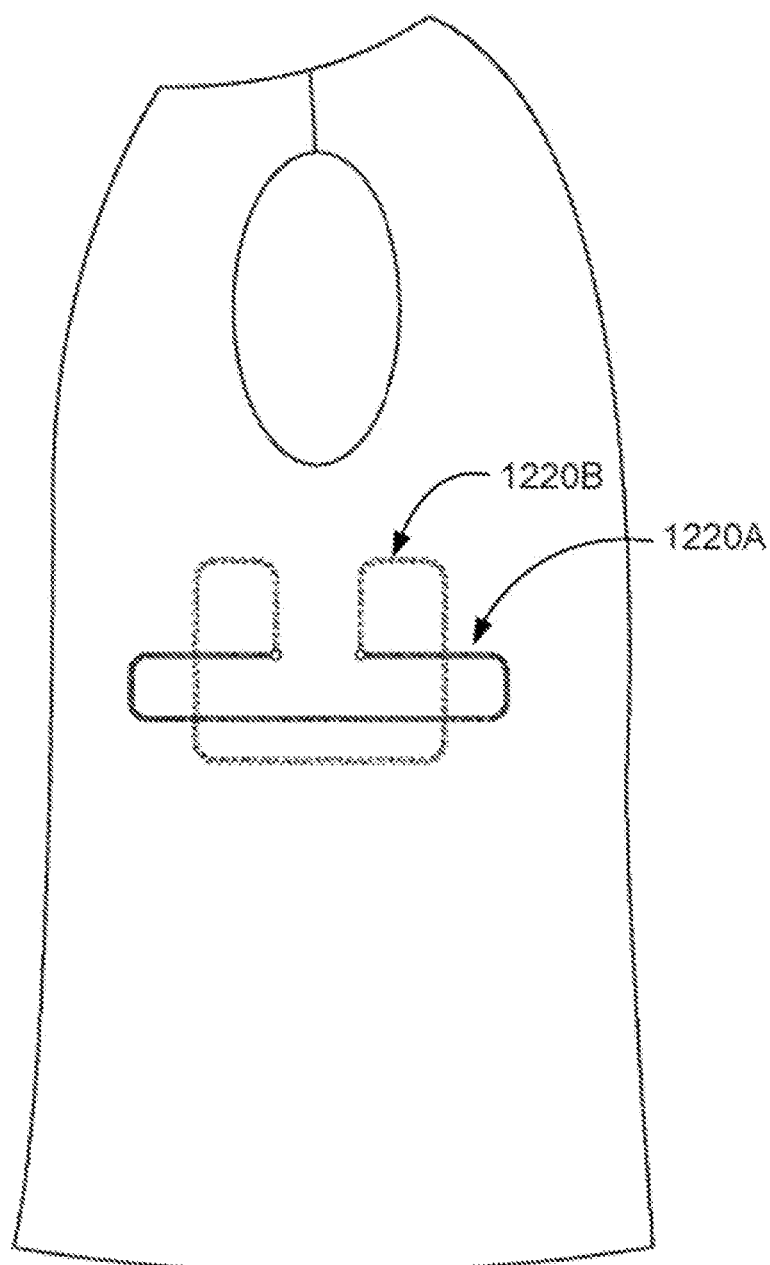
FIG. 12 is a schematic illustration showing a configuration of an elongate member, according to some embodiments.
Figure 13:
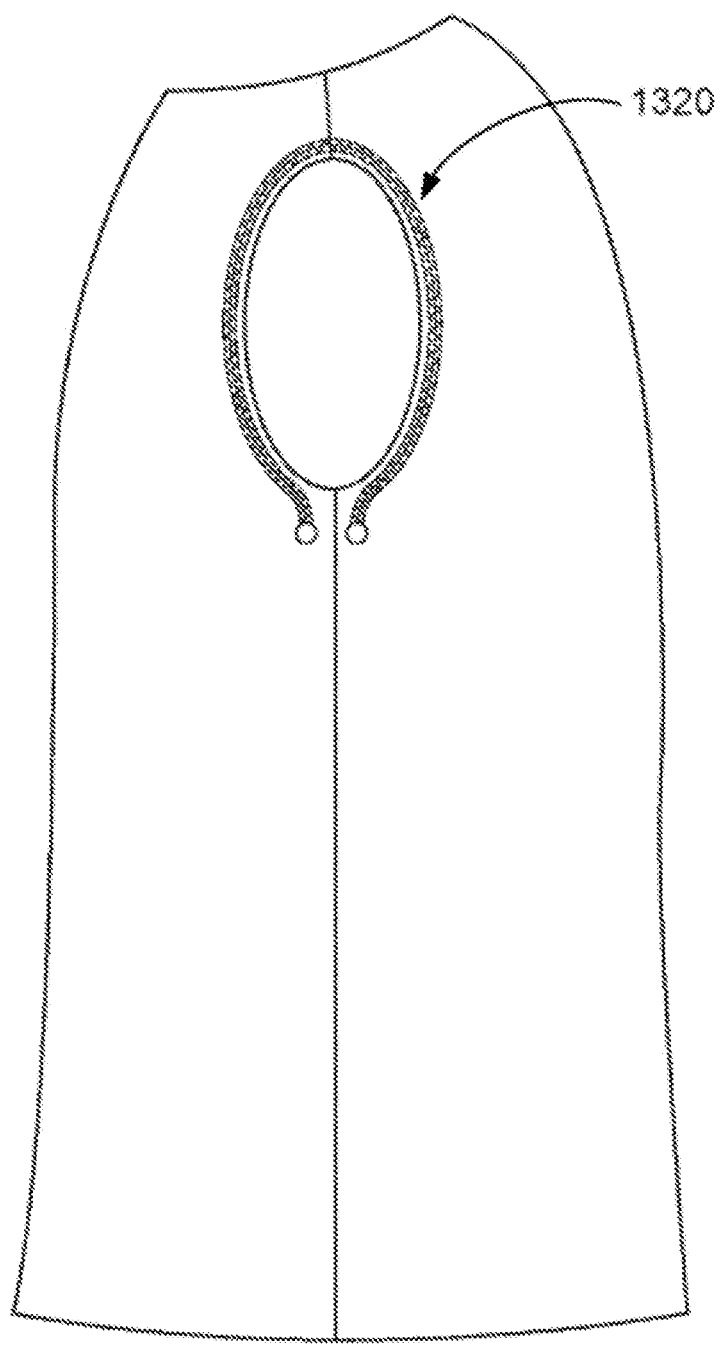
FIG. 13 is a schematic illustration showing a configuration of an elongate member, according to some embodiments.

FIGS. 11-16 are schematic illustrations showing configurations of elongate members with conductive wires coupled thereto, according to some embodiments. FIG. 11 shows a front view of a biosensing garment, according to an embodiment, with two example configurations of an elongate member (shape "1120A" and shape "1120B"). FIG. 12 shows a side view of a biosensing garment, according to an embodiment, with two example configurations of an elongate member (shape "1220A" and shape "1220B"). FIG. 13 shows a side view of a biosensing garment, according to an embodiment, with an example configuration of an elongate member 1320 that is disposed around a perimeter of an armhole of the biosensing garment.

FIG. 14 is a schematic illustration showing a folded configuration of a partially-constructed elongate member 1420, for incorporation into and/or use as a physiological sensor 1410, according to some embodiments. As shown in FIG. 14, a single conductive wire, having a continuous, substantially sinusoidal pattern, is coupled to the elongate member 1420, and is folded back over onto itself, thereby forming two sections (1440A and 1440 B) that overlay one another. The pattern of the conductive wire section 1440A (i.e., a top layer of the folded configuration, disposed along a first "pass" of the elongate member 1420, moving from right to left) may be said to have a periodicity of about 13.5 or 14 over distance D. The elongate member 1420 and conductive wire are folded at the left edge of FIG. 14, such that the elongate member continues, extending from left to right behind or beneath the top layer of the folded configuration (thereby forming a bottom layer of the folded configuration). This second "pass" of the elongate member 1420, moving from left to right, includes the conductive wire section 1440B (shown in bold, where 1440B is electrically and/or physically continuous with conductive wire section 1140A, i.e., conductive wire section 1440A and conductive wire section 1440B are part of the same conductive wire) coupled thereto, and the conductive wire section 1440B also has a continuous substantially sinusoidal pattern. The pattern of the conductive wire section 1440B may also be said to have a periodicity of about 13.5 or 14 over distance D. As such, the frequency and period of the entire conductive wire (including 1440A and 1440B) is substantially constant. However, as can be seen in FIG. 14, conductive wire sections 1440A and 1440B are out-of-phase with one another (e.g., about 180° out-of-phase). Depending upon where the fold is made in the elongate member 1420 and conductive wire, the conductive wire sections 1440A and 1440B may be in-phase with one another, substantially in-phase with one another, or out-of-phase with one another (e.g., by 45°, 90°, 180°, etc.). To complete the construction of the elongate member 1420 shown in FIG. 14, the conductive wire section 1440B would continue rightward, traversing the path shown by a dashed line. Such folded configurations can provide a smaller physical footprint of the elongate member, for example so that it is more readily incorporated into a physiological sensor, and/or so that closure mechanisms such as zippers and snaps in a biosensing garment can be actuated in the presence of the elongate member without said closure mechanisms interfering with or interrupting the continuity (e.g., including the electrical conductivity) of the conductive wire coupled to the elongate member, as described in further detail below.

Figure 15A:
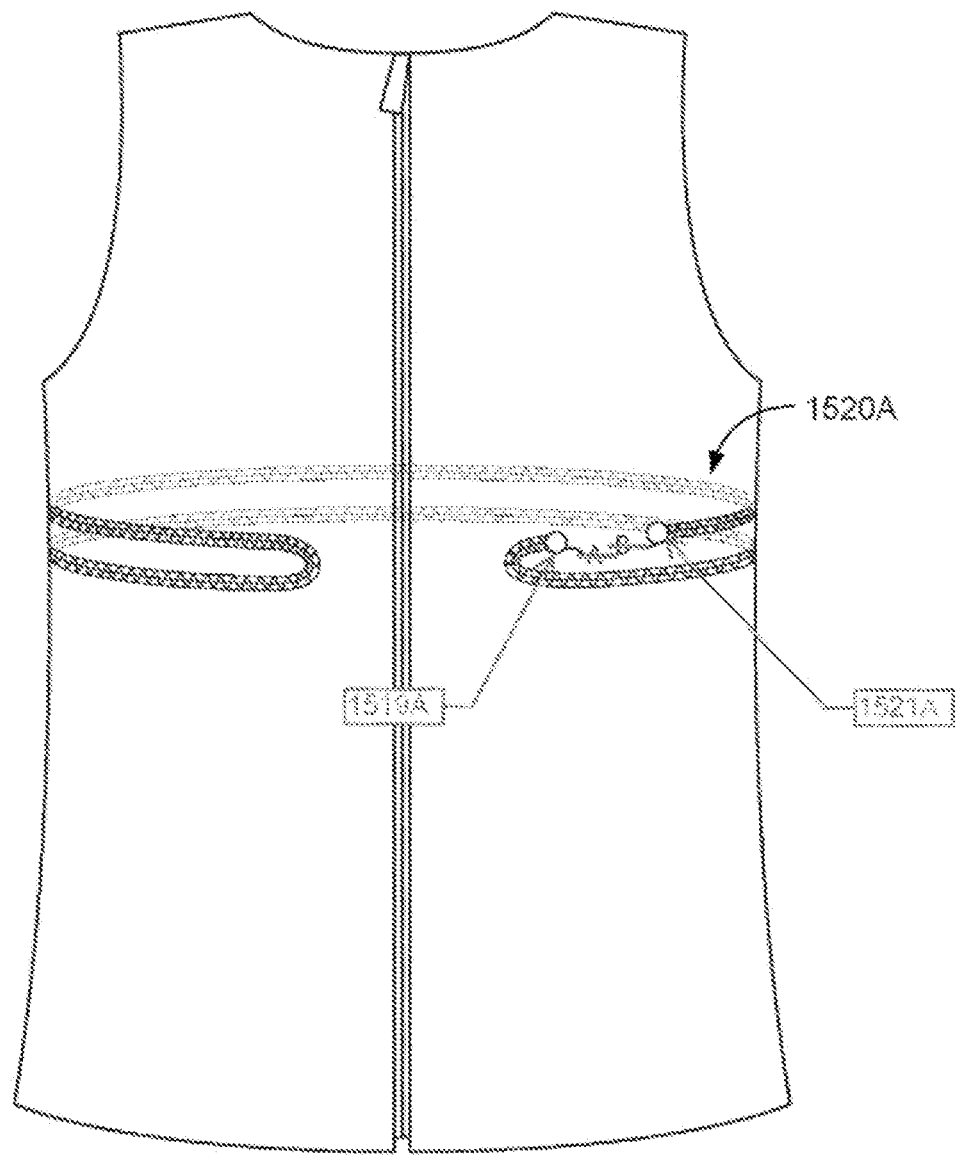
FIGS. 15A-15B are schematic illustrations showing configurations of an elongate member, according to some embodiments.

FIG. 15A shows a front view of a biosensing garment, according to an embodiment, having a vertically disposed zipper closure substantially centered on the front of the garment, and including a perspective view of an example configuration of an elongate member 1520A extending in an elongated loop shape around a portion of a circumference of the biosensing garment. As shown in FIG. 15A, an elongate member 1520A originates from a first connector 1519A on the front of the biosensing garment, extends in a first direction (to the left in FIG. 15A), and bends, in the plane of the garment, in a substantially "U" shape such that the elongate member 1520A continues in a second direction opposite the first direction (to the right in FIG. 15A). The elongate member 1520A continues circumferentially around the back of the biosensing garment (right to left in FIG. 15A) and onto the front of the biosensing garment, bending once again, in the plane of the biosensing garment, in a substantially "U" shape prior to reaching the zipper closure, again reversing its direction of travel (to the left in FIG. 15A). The elongate member 1520A continues circumferentially around the back of the biosensing garment (left to right in FIG. 15A) and onto the front of the biosensing garment where it terminates at a second connector 1521A. As such, the elongate member 1520A forms a complete loop, and traverses a substantial percentage of the circumference of the biosensing garment, without crossing the zipper closure. In the configuration of FIG. 15A, the elongate member 1520A may be said to have a planar, elongated loop shape, in which two sections of the elongate member 1520A are disposed parallel to one another (e.g., everywhere except at the bends and between connectors A and B) along a majority of the biosensing garment's circumference.

Figure 15B:
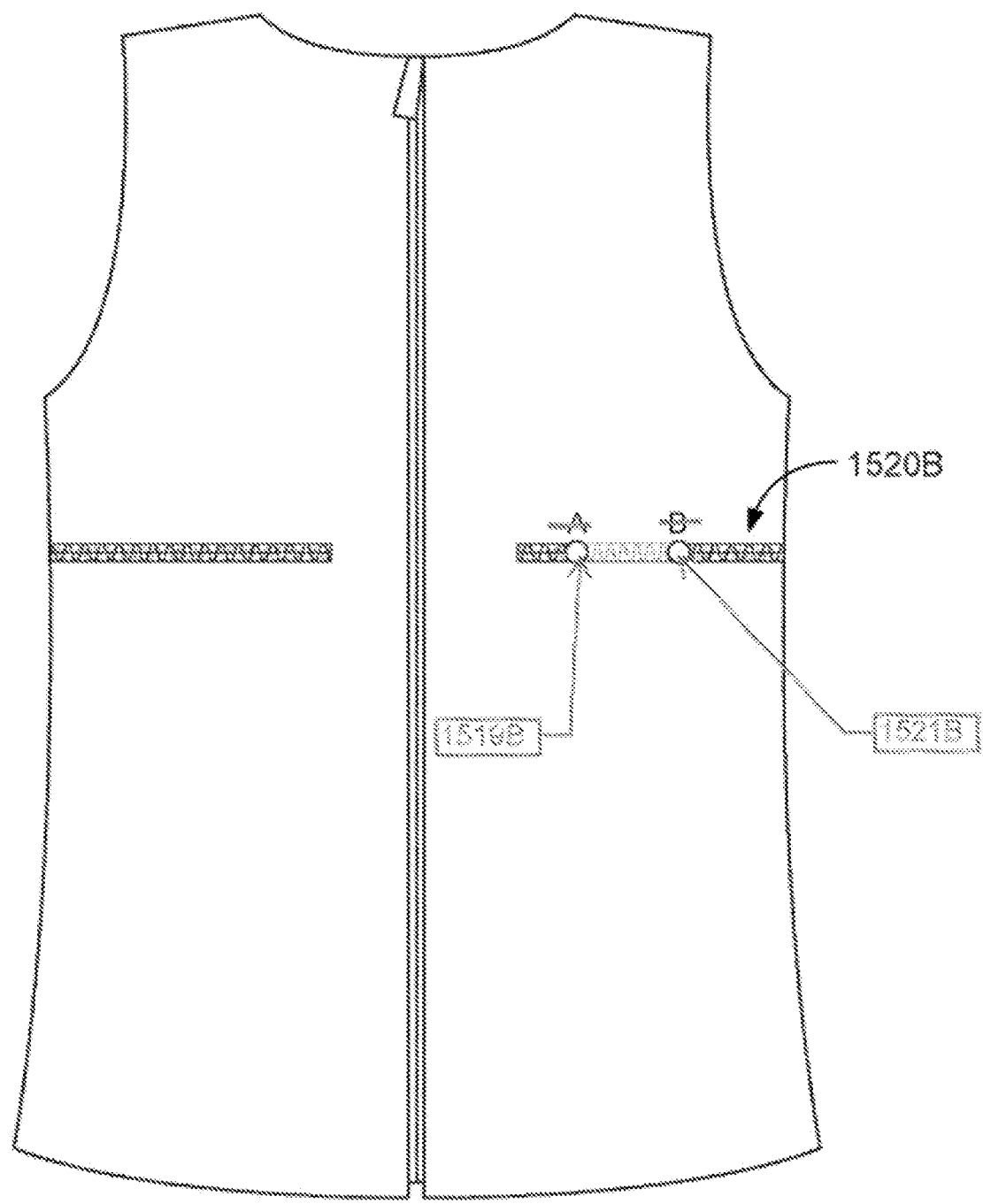

FIG. 15B shows a front view of a biosensing garment, according to an embodiment, having a vertically disposed zipper closure substantially centered on the front of the garment, and including an example configuration of an elongate member 1520B extending in a folded configuration around a portion of a circumference of the biosensing garment. As shown in FIG. 15B, an elongate member 1520B originates from a first connector 1519B on the front of the biosensing garment, extends in a first direction (to the left in FIG. 15B), and is folded back onto itself such that the elongate member 1520B continues in a second direction opposite the first direction (to the right in FIG. 15B). In other words, the elongate member 1520B includes a first portion extending from the first connector 1519B in the first direction, and a second portion extending in the second direction from the first portion to the second connector 1521B. The elongate member 1520B continues circumferentially around the back of the biosensing garment (right to left in FIG. 15B) and onto the front of the biosensing garment, folded back onto itself once again prior to reaching the zipper closure, again reversing its direction of travel (to the left in FIG. 15B). The elongate member 1520B continues circumferentially around the back of the biosensing garment (left to right in FIG. 15B) and onto the front of the biosensing garment where it terminates at the second connector 1521B. As such, the elongate member 1520B forms a complete loop, and traverses a substantial percentage of the circumference of the biosensing garment, without crossing the zipper closure. In the configuration of FIG. 15B, the elongate member 1520B may be said to have a folded, bilayer, or "overlay" configuration (e.g., everywhere except between connectors 1519B and 1521B), in which two sections of the elongate member 1520B are disposed parallel to and atop one another along a majority of the biosensing garment's circumference.

In some embodiments, the first portion of the elongate member 1520B has a length approximately the circumference of the biosensing garment. In some embodiments, the first portion of the elongate member 1520B has a length less than the full circumference of the biosensing garment. In some embodiments, the first portion of the elongate member 1520B is less than about 99%, less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, or less than about 5% of the circumference of the biosensing garment.

In some embodiments, a vertically disposed zipper closure is disposed on the back of the garment instead of, or in addition to, the front of the garment. In some embodiments, a zipper closure is included in the garment in an orientation other than vertical (e.g., horizontal, diagonal, etc.), and/or may extend only partway across the garment along its direction of travel.

Figure 16:
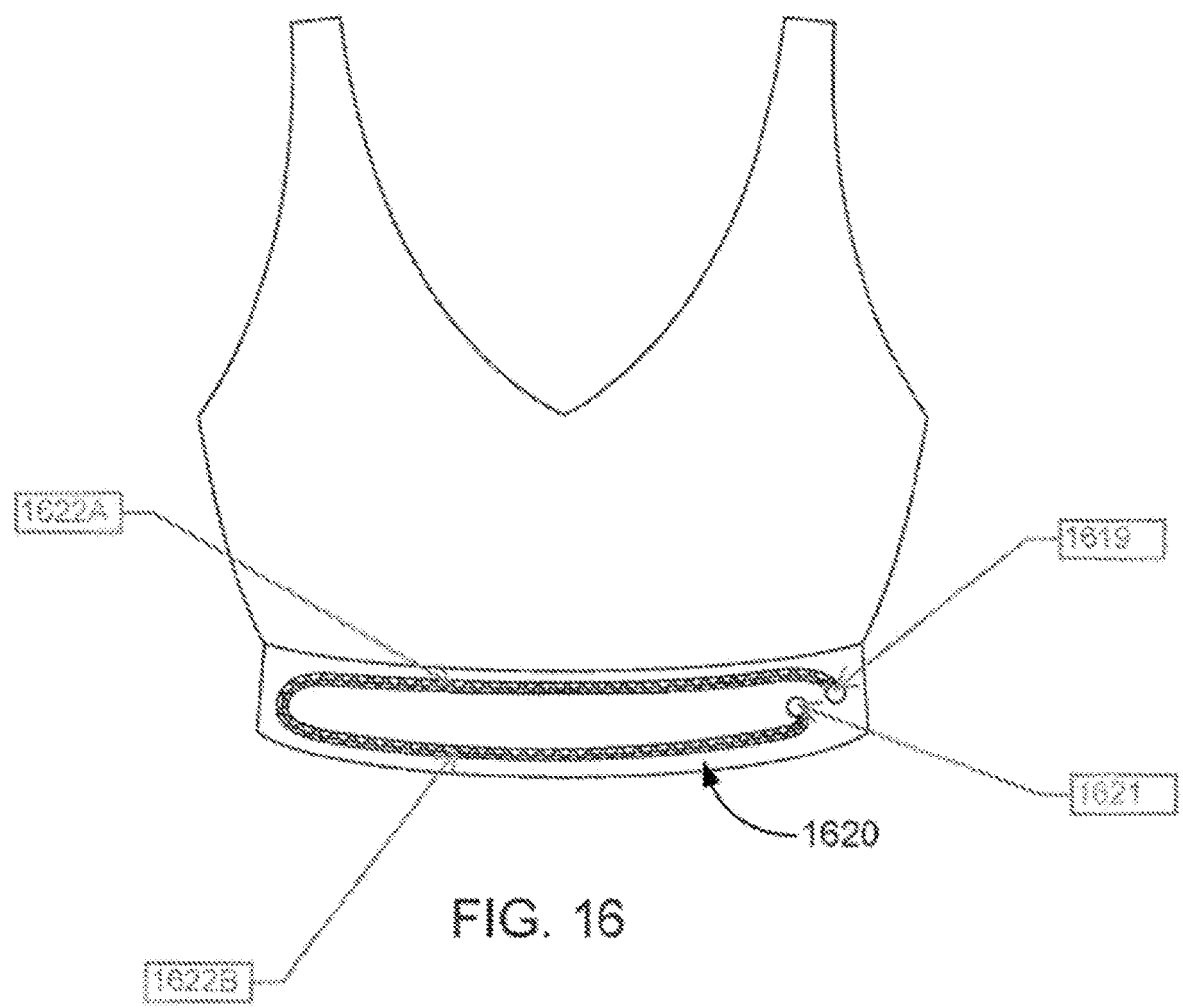
FIG. 16 is a schematic illustration showing a configuration of an elongate member, according to some embodiments.

FIG. 16 shows a front view of a biosensing garment (e.g., a biosensing bra) having a loop-shaped elongate member 1620 disposed in a lower band (e.g., wholly disposed within a "front" portion of the lower band of the biosensing bra), and having a hook (e.g., "hook-and-eye") opening in the back (e.g., instead of a zip opening in the front).

In some embodiments, an apparatus, such as a biosensing garment, can include an elongate member 1620 defining a longitudinal axis and configured to be stretchable along the longitudinal axis. In some embodiments, the elongate member 1620 includes a plurality of substantially parallel elastic members. In some embodiments, a conductive member comprising an electrical conductor can be fixedly coupled to at least one of the plurality of substantially parallel elastic members. In some embodiments, the conductive member can be disposed in a regular pattern along the longitudinal axis of the elongate member 1620 and configured to move between a first configuration and a second configuration.

In some embodiments, an apparatus, such as a biosensing garment, can include a plurality of substantially parallel elastic members disposed along an axis and configured to be stretchable along the axis. In some embodiments, a conductive member is disposed in a regular pattern and fixedly coupled to at least one of the plurality of substantially parallel elastic members. In some embodiments, the conductive member is configured to move between a first configuration and a second configuration.

In some embodiments, the conductive member has a first inductance value in the first configuration, and a second inductance value in the second configuration. In some embodiments, the regular pattern of the conductive member is a curved pattern. In some embodiments, the curved pattern of the conductive member is substantially sinusoidal.

In some embodiments, a biosensing garment can include a first connector coupled to a first end of the elongate member and a second connector coupled to a second end of the elongate member, and the first connector is disposed proximate the second connector to form an open loop. In some embodiments, the open loop is disposed in at least one of a substantially circular shape, a substantially oval shape, a substantially square shape, a substantially rectangular shape, and an irregularly shape.

In some embodiments, the elongate member 1620 includes a first portion 1622A and a second portion 1622B. In some embodiments, a first connector 1619 is coupled to a first end or a first portion of the elongate member, and a second connector 1621 is coupled to a second end or a second portion of the elongate member. The first connector 1619 and/or first portion 1622A can be disposed proximate the second connector 1621 and/or second portion 1622B thereby forming an open loop. In some embodiments, the first portion 1622A can extend from the first connector 1619 in a first direction, and the second portion 1622B can extend in a second direction from the first portion 1622A to a second connector 1621. In some embodiments, the second direction is opposite the first direction. Although the first portion 1622A and second portion 1622B are shown "separated" from each other in FIG. 16, the first portion 1622A and second portion 1622B can at least partially overlap each other. In other words, in some embodiments, the second portion 1622B can be folded back onto the first portion 1622A. In some embodiments, the first portion 1622A is disposed substantially parallel to the second portion 1622B. In some embodiments, the first portion 1622A is disposed non-zero distance from the second portion 1622B. In some embodiments, the first portion 1622A and the second portion 1622B are disposed substantially overlapped, similar to the illustration as shown in FIG. 15B.

In some embodiments, at least one of the first portion 1622A and the second portion 1622B of the elongate member 1620 has a length approximately the circumference of the biosensing garment. In some embodiments, at least one of the first portion 1622A and the second portion 1622B of the elongate member 1620 has a length less than the full circumference of the biosensing garment. In some embodiments, at least one of the first portion 1622A and the second portion 1622B of the elongate member 1620 is less than about 99%, less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, or less than about 5% of the circumference of the biosensing garment.

Figure 17A:
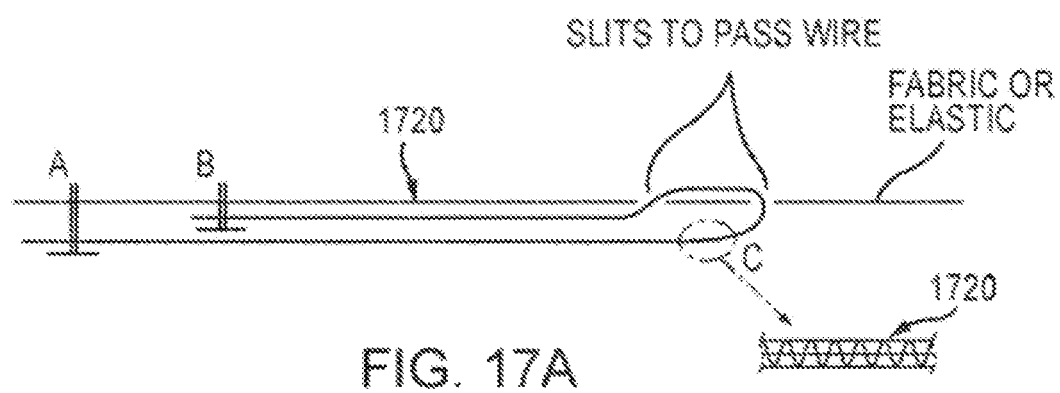
FIGS. 17A-17B are schematic illustrations showing cross-sectional views of a folded configuration of an elongate member, according to some embodiments.
Figure 17B:
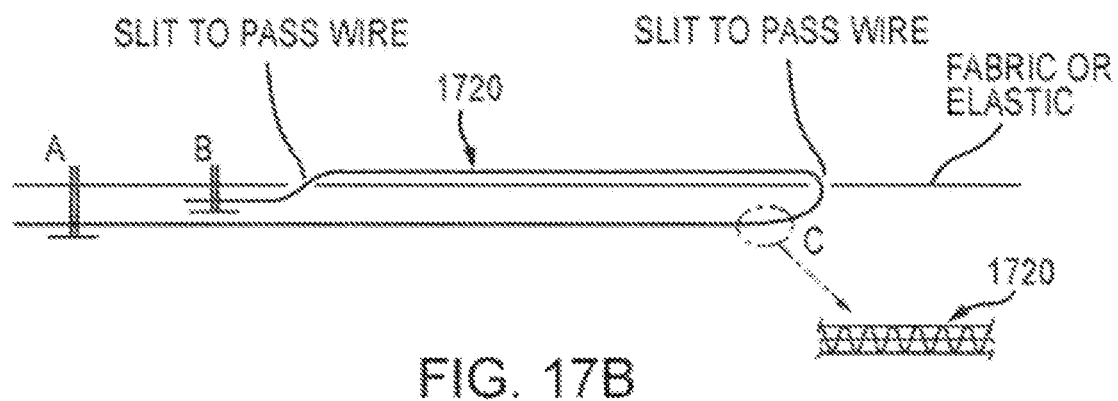

FIGS. 17A-17B are schematic illustrations showing cross-sectional views of a folded configuration of an elongate member bearing a conductive wire (e.g., a RIP sensor), according to some embodiments. As shown in FIGS. 17A and 17B, an elongate member 1720 (a detail view of which is shown at sections "C") is disposed adjacent to a first surface of a fabric or elastic substrate (e.g., a biosensing garment or portion thereof) and passes through two slits in said fabric or elastic substrate such that at least a portion of the elongate member 1720 is disposed on a second surface of the fabric or elastic substrate, and such that the elongate member 1720 folds back on itself. Described sequentially, the elongate member 1720 is connected to connector "A," then: (1) extends in a first direction substantially parallel to a first surface of the fabric or elastic substrate; (2) passes through a first slit in the fabric or elastic substrate, forming a fold in the elongate member 1720; (3) extends in a second direction, opposite the first direction, adjacent and substantially parallel to a second surface of the fabric or elastic substrate; (3) passes through a second slit in the fabric; (4) extends in the second direction, adjacent and substantially parallel to the first surface of the fabric or elastic substrate; and (5) is connected to connector "B." As shown in FIGS. 17A and 17B, the elongate member 1720 has a modified configuration as compared with the planar configurations of FIGS. 15 and 16. Instead of looping the elongate member around a specific shape (circle, rectangle etc.), where the loop forms a specific shape and surface area, the elongate member of FIGS. 17A and 17B is folded and relayed back along substantially the same axis (i.e., multilayered, or "overlayed"). In the configurations of FIGS. 17A and 17B, the spacing between the slits determines the proportion of the elongate member 1720 that is disposed on/adjacent to the first surface of the fabric or elastic substrate and the proportion of the elongate member that is disposed on/adjacent to the second surface of the fabric or elastic substrate. In some embodiments, the elongate member includes more than one fold (e.g., 2 or 3 folds).

Figure 18A:
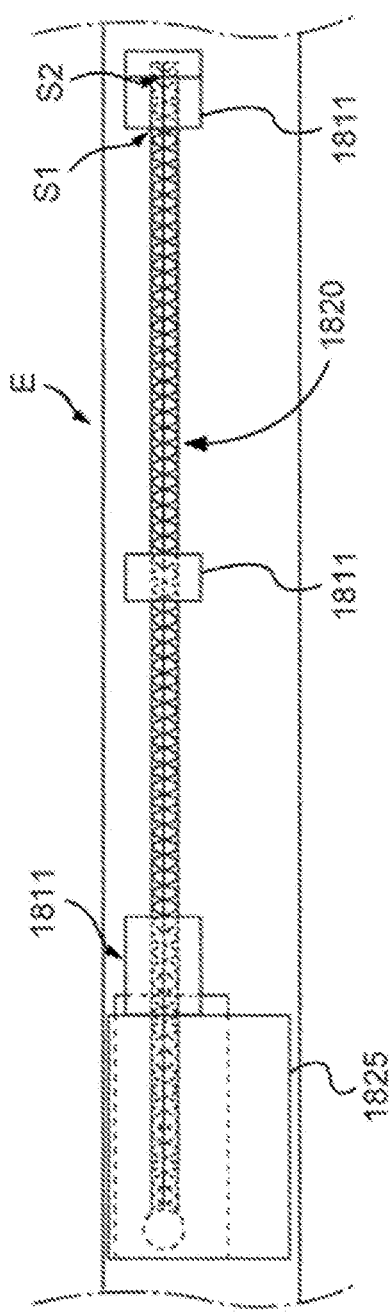
FIGS. 18A-18B are schematic illustrations showing a folded configuration of an elongate member incorporated into a garment, according to an embodiment.
Figure 18B:
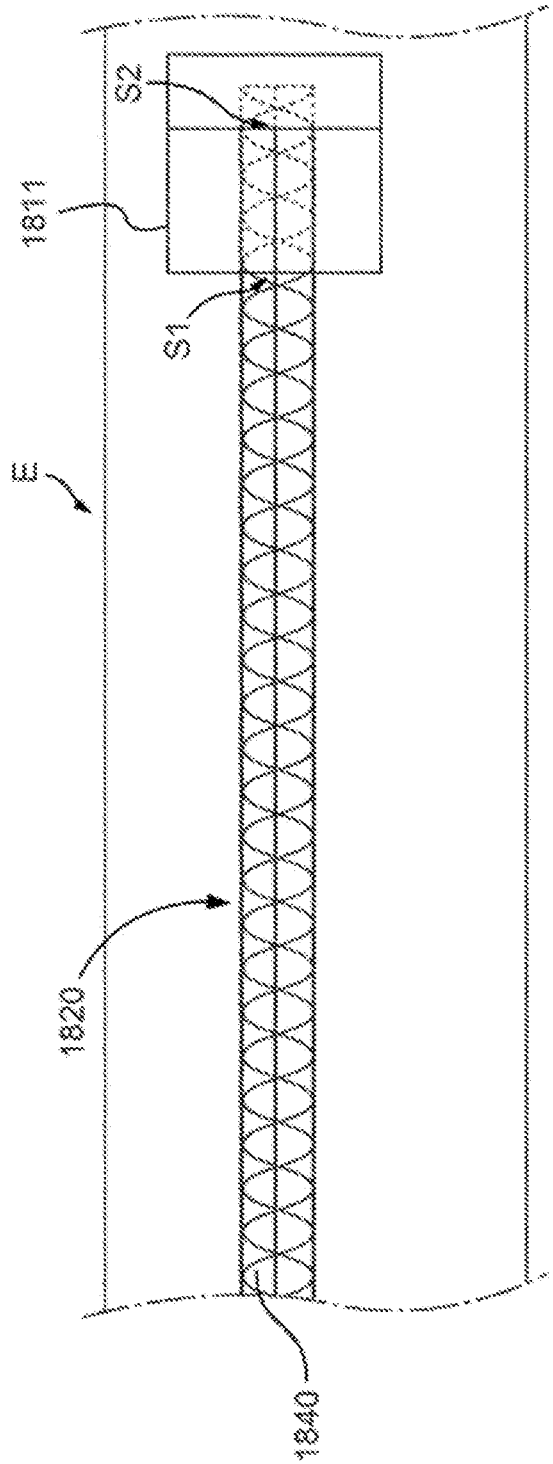

FIGS. 18A-18B are schematic illustrations showing planar views of a folded configuration of an elongate member bearing a conductive wire incorporated into a garment (or portion thereof), the elongate member having overlaying sections, according to some embodiments. As shown in FIG. 18A, the elongate member 1820, including a conductive wire 1840, is folded and looped through slits "51" and "S2" in an elastic band "E," and relayed back along the same axis, such that first and second sections of the elongate member 1820 are substantially overlapping. As shown in FIGS. 18A and 18B, the elongate member can be supported by one or more fabric or thermoplastic portions 1811 and 1825, for example, that are stitched into, adhered to, or otherwise secured to the elastic band "E." The length of the folded elongate member 1820 can be any appropriate length, e.g. 10 cm, 20 cm, 30 cm, or any other desired length, depending on the application. The overlapping sections of conductive wire 1840 (i.e., the portion of conductive wire 1840 that extends from left to right prior to folding and the portion of conductive wire 1840 that extends from right to left after folding) are shown in FIGS. 18A and 18B to be out-of-phase with one another (i.e., −180° out-of-phase) by a substantially constant amount across the entire length of the elongate member 1820. However, depending upon where the fold is made in the elongate member 1820 and conductive wire, the conductive wire sections may be in-phase with one another, substantially in-phase with one another, or out-of-phase with one another (e.g., by 45°, 90°, 180°, etc.).

FIGS. 18C-18D are schematic illustrations showing planar views of a further folded configuration of an elongate member bearing a conductive wire incorporated into a garment (or portion thereof), the elongate member having alternating sections, according to an embodiment. As shown in FIG. 18C, the elongate member 1820, including a conductive wire 1840 electrically connected to connector 1819, extends in a sinusoidal or periodic pattern (from left to right in FIG. 18C) and is folded back on itself (e.g., at the right edge of the elongate member 1810 in FIGS. 18C and 18D) such that it is relayed back along the same axis (from right to left in FIG. 18C), also in a sinusoidal or periodic pattern, and such that first and second sections of the elongate member 1820 (e.g., top and bottom sections) are only partially (e.g., periodically) overlapping. The conductive wire coupled to elongate member 1820 is electrically connected to connector 1821. As shown in FIGS. 18C and 18D, the elongate member 1820 can be supported by one or more fabric or thermoplastic portions 1811 and 1825, for example, that are stitched into, adhered to, or otherwise secured to an elastic band "E." The length of the folded elongate member 1820 can be any appropriate length, e.g. 10 cm, 20 cm, 30 cm, or any other desired length, depending on the application. In some embodiments, both the elongate member 1820 and the conductive wire 1840 coupled thereto are "folded," such that a single elongate member and a single conductive wire are disposed between connectors 1819 and 1821. In other embodiments, the elongate member 1820 comprises two separate segments (e.g., a top segment and a bottom segment) and a single conductive wire that is folded as it passes from the first elongate member segment into the second elongate member segment.

FIGS. 19A-19B are schematic illustrations showing planar views of a folded configuration of an elongate member bearing a conductive wire incorporated into a garment (or portion thereof), the elongate member having parallel sections, according to some embodiments. As shown in FIG. 19A, the elongate member 1920, including a conductive wire 1940, traverses a longitudinal path along an elastic band "E," and is folded (e.g., by passing through slits in the elastic band "E") and relayed back along a substantially parallel axis, such that first and second sections of the elongate member 1920 are substantially parallel and non-overlapping. As shown in FIGS. 19A and 19B, the elongate member 1920 can be supported by one or more fabric or thermoplastic portions 1911 and 1925, for example, that are stitched into, adhered to, or otherwise secured to the elastic band "E." The length of the folded elongate member 1920 can be any appropriate length, e.g. 10 cm, 20 cm, 30 cm, or any other desired length, depending on the application.

FIGS. 19C-19D are schematic illustrations showing a looped wire configuration of an elongate member bearing a conductive wire incorporated into a garment (or portion thereof), according to an embodiment. In the configuration of FIGS. 19C-19D, instead of having a folded elongate member or having the elongate members looped around a specific shape, the conductive wire itself is interweaved back and forth within the same assembly (e.g., a single elongate member 1920). The length and height (amplitude) of the conductive wire can be determined based on the desired application. As shown in FIG. 19C, a single elongate member 1920 includes a single conductive wire that originates at connector 1919, traverses a length "L" of a longitudinal axis of an assembly (e.g., an elastic band, a segment of fabric, a garment or portion thereof, etc.) with a sinusoidal or periodic pattern, and is then woven, affixed, folded or otherwise made to traverse back along the length "L" of the longitudinal axis of the assembly for connection at connector 1921. The period of the conductive wire of FIG. 19C for each traversal of the length "L" repeats approximately 8.5 times.

In FIG. 19D, a single elongate member 1920 includes five elastic members and a single conductive wire that originates at connector 1919, traverses a length "L" of a first longitudinal axis of the elongate member 1920 (i.e., spanning the bottom three elastic members of the elongate member 1920) with a sinusoidal or periodic pattern, and is then woven, affixed, folded or otherwise made to traverse back along the length "L" of a second longitudinal axis of the elongate member 1920 (i.e., spanning the top three elastic members of the elongate member 1920) for connection at connector 1921. The period of the conductive wire of FIG. 19D for each traversal of the length "L" repeats approximately 8.25 times.

FIGS. 20A-20H show components for use in an assembly process, according to an embodiment. Some or all of the materials described with reference to FIGS. 20A-20H can be used for assembly steps of the present disclosure, for example such as those discussed below with reference to FIGS. 21A-21M. FIG. 20A depicts a breathing cable attachment 2011, which may comprise thermoplastic polyurethane ("TPU") or any other type of material that is suitable for lamination. The breathing cable attachment can be colored (e.g., black) or transparent. In some embodiments, the breathing cable attachment 2011 has a width of about 25 mm and a height of about 30 mm. As shown in FIG. 20A, the breathing cable attachment 2011 has a fold line down its middle, e.g., along a longitudinally extending centerline thereof (see, e.g., the dashed line in FIG. 20A).

FIG. 20B depicts a middle part with double holes 2013, which may comprise thermoplastic polyurethane ("TPU") or any other type of material that is suitable for lamination. Each hole of the double holes 2013 can have a diameter of about 3 mm, or any other suitable diameter depending on the snap that is used. The middle part with double holes 2013 can be colored (e.g., black) or transparent. In some embodiments, the middle part with double holes 2013 has a width of about 60 mm and a height of about 20 mm.

FIG. 20C depicts a middle part with single holes 2015, which may comprise TPU or any other type of material that is suitable for lamination. Each of the single holes 2015 can have a diameter of about 3 mm, or any other suitable diameter depending on the snap that is used. The middle part with single holes 2015 can be colored (e.g., black) or transparent. In some embodiments, the middle part with single holes 2015 has a width of about 60 mm and a height of about 20 mm.

FIG. 20D depicts a support bridge 2017, which may comprise PET film, PA, PTFE, PE (HDPE, LDPE, MDPE, UHMWPE, ULMWPE), PP or other suitable plastic.

FIG. 20E depicts a conductive tape ring 2019 which may comprise any conductive tape, such as silver tape, copper tape, aluminum tape, carbon conductive tape, single-sided or double-sided tapes, e,g, having XY or XYZ axis conductivity, conductive fiber or particle filled adhesives and/or the like. In some embodiments, the conductive tape ring 2019 has an outer diameter of about 14 mm or other suitable diameter depending upon the snap size being used. In some embodiments, the conductive tape ring 2019 has an inner hole diameter of about 3 mm or other suitable diameter depending upon the snap size being used. In some embodiments, the conductive tape ring 2019 is double-sided and/or comprises one or more "liner sheets" (for example, to protect one or more adhesive surfaces thereof).

FIG. 20F depicts a PET film ring 2021 comprising PET. In some embodiments, the PET film ring 2021 has an outer diameter of about 14 mm or other suitable diameter depending upon the snap size being used. In some embodiments, the PET film ring 2021 has an inner hole diameter of about 3 mm or other suitable diameter depending upon the snap size being used.

FIG. 20G depicts a garment TPU segment 2023. The garment TPU segment 2023 can be transparent, or can be colored (e.g., black). In some embodiments, the garment TPU segment 2023 has a width of about 90 mm and a height of about 15 mm.

FIG. 20H depicts a final cover 2025, which may comprise thermoplastic polyurethane ("TPU") or any other type of material that is suitable for lamination. The final cover 2025 can be colored (e.g., black) or transparent. In some embodiments, the final cover 2025 has a width of about 70 mm and a height of about 30 mm.

In some embodiments, the breathing cable attachment 2011, the middle part with double holes 2013, the middle part with single holes 2015, the garment TPU segment 2023 and/or the final cover 2025, and/or any other TPU segment (or "membrane") used in assembling the biosensing garment(s) described herein, have one or more release layers (also referred to herein as "backing papers" disposed thereon (e.g., on both sides), to protect adjacent surfaces during assembly steps involving the application of heat. Such paper layers can be removed at some point after lamination such that no paper remains in the final construction of the biosensing garment. In some embodiments, the breathing cable attachment 2011, the middle part with double holes 2013, the middle part with single holes 2015, the garment TPU segment 2023 and/or the final cover 2025, and/or any other TPU segment (or "membrane") used in assembling the biosensing garment(s) described herein, is double-sided (i.e., can be laminated on both sides and/or includes a backing paper on one or both sides). In some embodiments, instead of or in addition to TPU, a different polyurethane plastic or other suitable strain relief material is used for one or more of the foregoing components. In some embodiments, using plastic and/other laminating materials allows the connector regions to be flexible but not stretchable.

In some embodiments, an assembly process for a biosensing garment begins with measuring and cutting a breathing wire to a desired width. For example, if assembling a biosensing brassiere ("bra"), the width of a bra may be calculated as follows:

((BRA WIDTH*2)+2 cm)+5%;

and if assembling a biosensing shirt, the width of a shirt may be calculated as follows:

((SHIRT WIDTH*2)+2 cm)+3.5%.

Subsequent assembly steps are described below, with reference to FIGS. 21A-21M.

FIG. 21A shows a first end of a physiological sensor 2110 (produced as described herein) near which a "first" segment of TPU (breathing cable attachment 2111) has been laminated (e.g., by application of heat, or "heat press"). As shown in FIG. 21A, the breathing cable attachment 2111 has been placed about 2.5 cm from an end of the physiological sensor 2110. In some embodiments, the breathing cable attachment 2111 is folded along a fold line (see, e.g., FIG. 20A) such that it envelops the physiological sensor 2110, covering both faces thereof, while ensuring that the physiological sensor 2110 itself is not folded. A further breathing cable attachment 2111 can be positioned at the opposite end of the physiological sensor 2110 and attached in the same manner as described with reference to FIG. 21A. The breathing cable attachments 2111 should be well-bonded (i.e., bonded "through") to the cable such that the conductive wire 2140 is not able to move inside the breathing cable attachments 2111 when the physiological sensor 2110 is pulled or stretched.

A portion of each of the end of the physiological sensor 2110 depicted in FIG. 21A may then be further cut (if needed), a segment of the textile portions (e.g., the elastic members) of the physiological sensor 2110 removed (e.g., by cutting and pulling away), and the conducting wire 2140 insulation (if present) stripped (see, e.g., location "S" in FIG. 21B). As shown in FIG. 21B, the conducting wire 2140 can be stripped such that there is about 0.5 cm of insulation intact that extends beyond the end of the respective breathing cable attachment 2111.

Figure 21C:
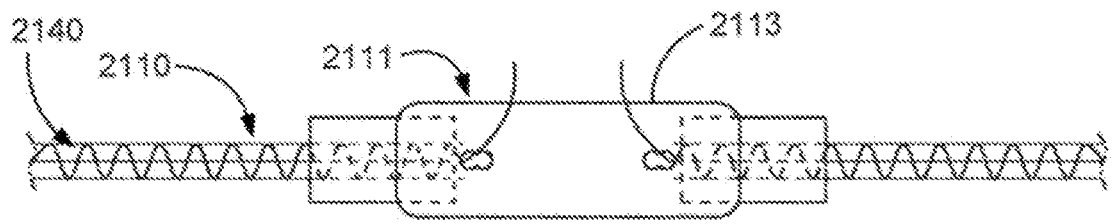
Figure 21D:
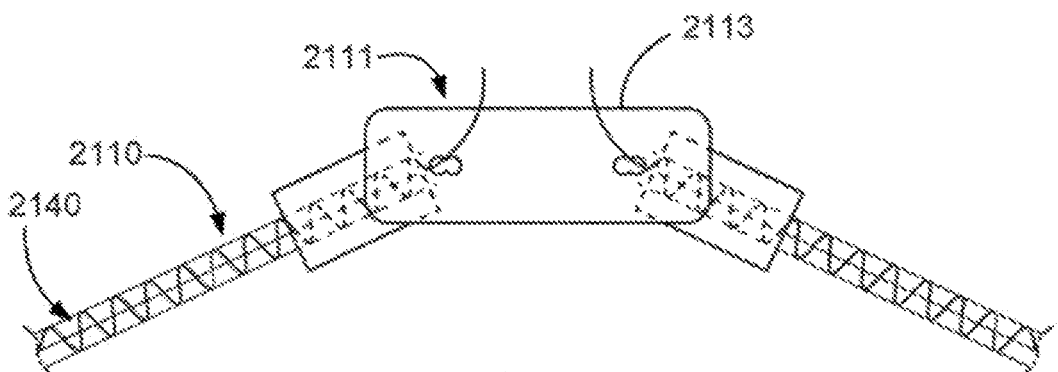
Figure 21E:
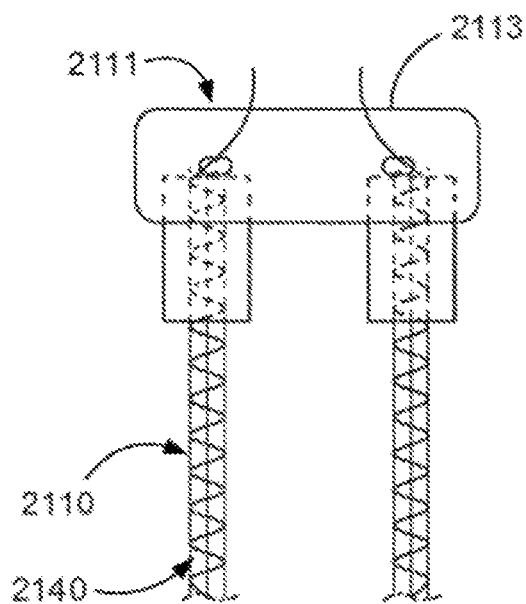

As shown in FIG. 21C, the stripped wires are fed through the outermost holes of a middle part with double holes 2113 (e.g., having its backing paper removed from a face to be bonded), and both breathing cable attachments 2111 are then laminated (e.g., ironed such that the wires remain in the outer holes) at least partially to the middle part with double holes 2113. In some embodiments, a backing paper disposed on the not-yet-bonded face of the middle part with double holes 2113 is left in place at this stage in the process. The lamination of the breathing cable attachments 2111 to the middle part with double holes 2113 physically secures them to one another, and can be done at an angle (see FIGS. 21D and 21E), for example if necessary or desired for subsequent assembly steps (e.g., based upon the design). For example, the lamination can be done at any angle (e.g., with respect to a longitudinal axis of the further, elongate TPU segment) required by the design, e.g., about 25 degrees, about 30 degrees, about 45 degrees, about 90 degrees, etc.

Figure 21F:
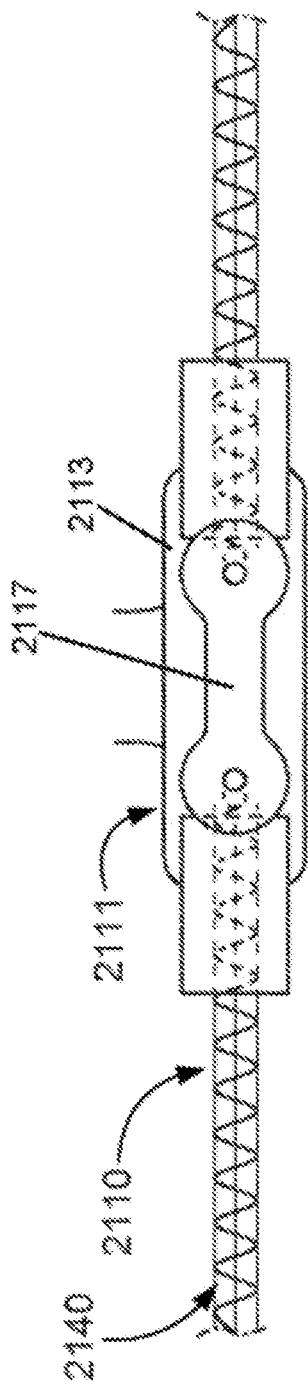
Figure 21G:
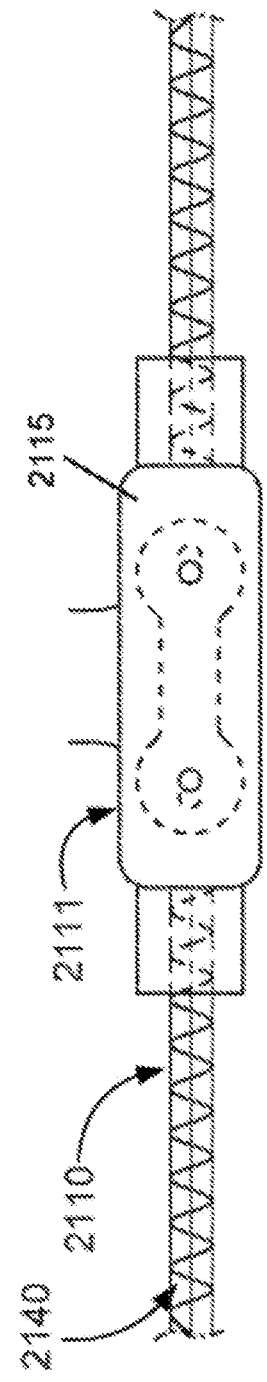
Figure 21H:
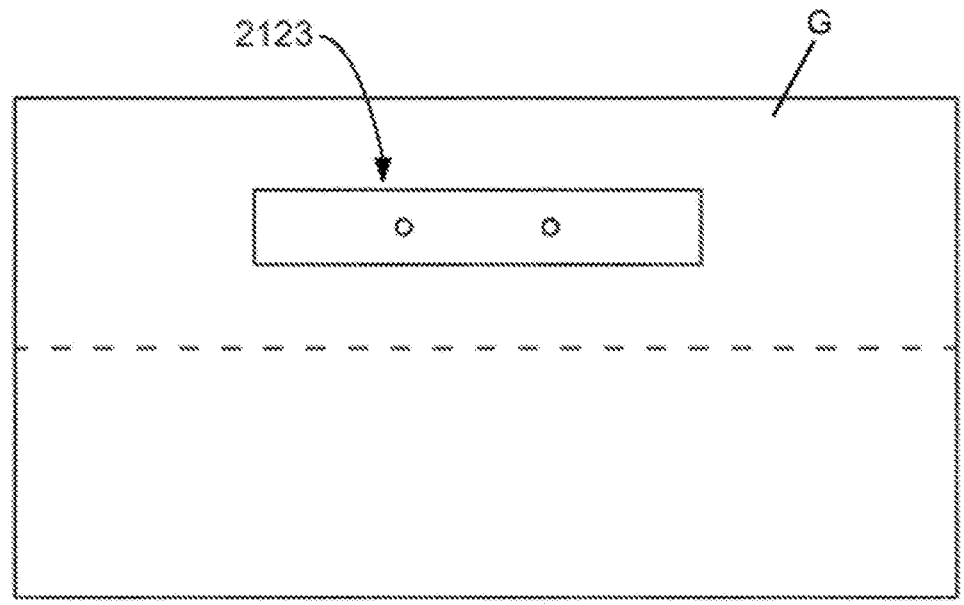

Next, an elongate (and, optionally, rigid) support bridge 2117 (shown in FIG. 21F), also bearing holes therethrough, is placed on the side of the middle part with double holes 2113 that is opposite where the exposed conductor ends have been fed through, and corresponding holes of the support bridge 2117 and the middle part with double holes 2113 (i.e., the "innermost" holes of the middle part with double holes 2113, as shown in FIG. 21F) are substantially aligned. The support bridge 2117 is then laminated to the middle part with double holes 2113 by applying heat (e.g., ironing or "heat press"), and a middle part with single holes 2115, comprising two holes, is positioned on top of the support bridge 2117, substantially aligned with the middle part with double holes 2113 (e.g., the innermost holes of the middle part with double holes 2113 are aligned with the holes of the middle part with single holes 2115), and laminated (again, optionally, with the assistance of a paper laminating sheet that is subsequently removed) thereto, resulting in the assembly (or "breathing cable structure") shown in FIG. 21G.

Figure 21I:
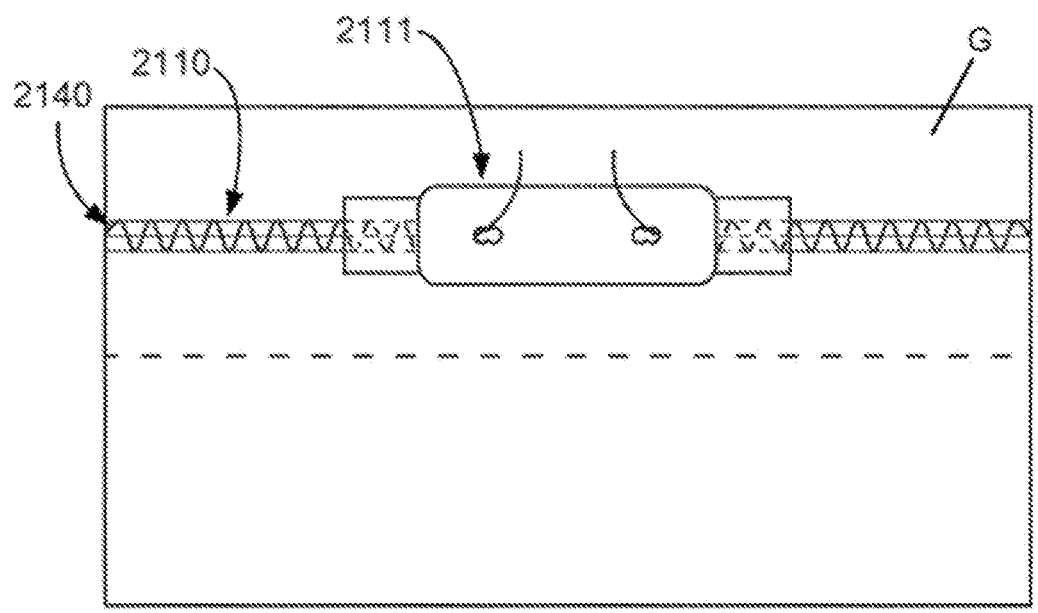

Separately, a garment TPU segment 2123 is laminated onto a desired garment or fabric section (see "G" in FIGS. 21H-21M), for example, on a "reverse" or interior side of a garment, and holes (corresponding with the holes of garment TPU segment 2123) are made through the fabric of the garment G for subsequent placement of snaps or other connector hardware, such as a hook connector, a Velcro® based connector, or the like. The assembly (or "breathing cable structure" of FIG. 21G) is placed onto the garment TPU segment 2123 that has been applied to the garment G, the holes are aligned, and the assembly is laminated to the garment TPU segment 2123 (again, optionally, with the assistance of a paper laminating sheet, after which lamination, the paper is removed). The result is shown in FIG. 21I.

Figure 21J:
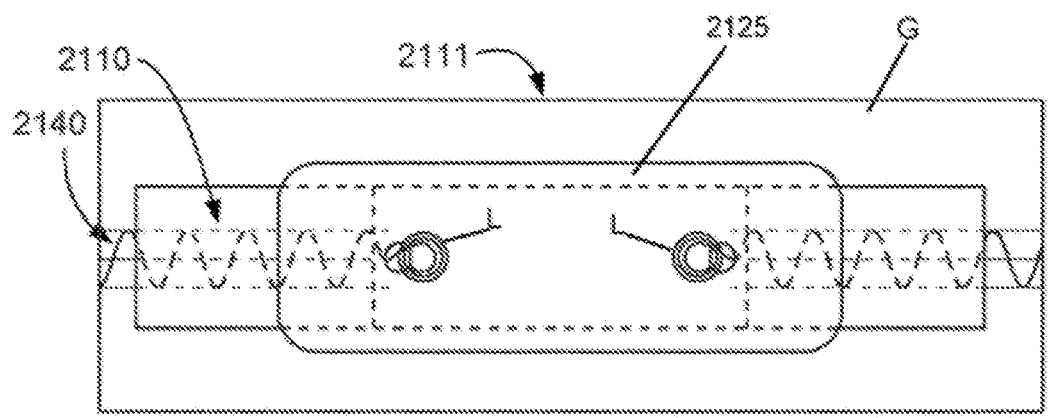

Turning now to FIG. 21J, the backing paper of the middle part with double holes 2113 is removed, and the exposed wire ends protruding through the outer holes of the middle part with double holes 2113 are twisted/coiled into loops "L" about the innermost holes of the middle part with double holes 2113.

Figure 21K:
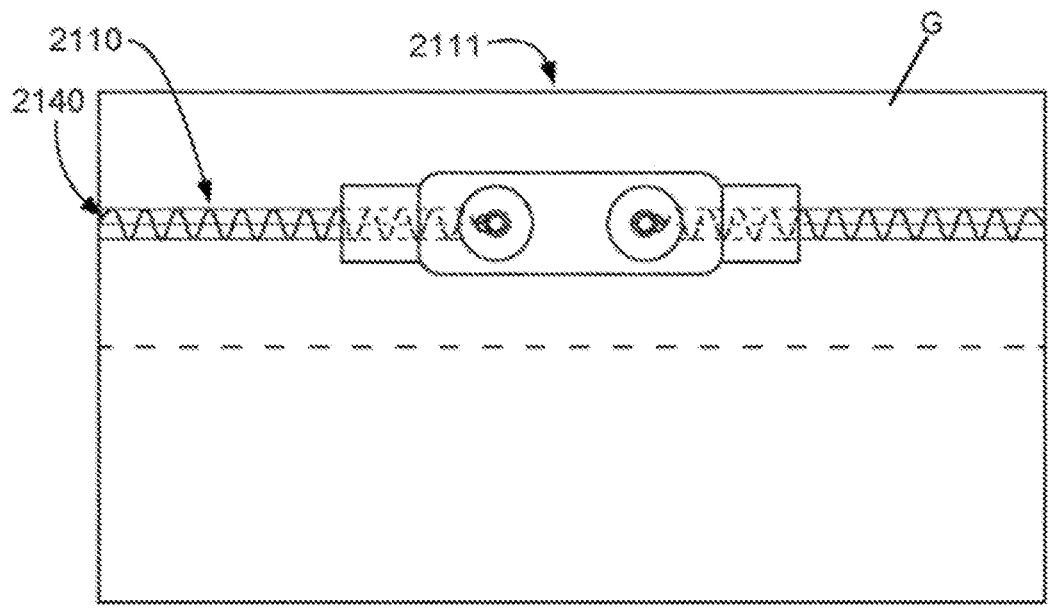

As shown in FIG. 21K, a first liner sheet is removed from each of two conductive tape rings 2119 to reveal bare adhesive faces thereof, and the bare adhesive faces of the conductive tape rings 2119 are positioned atop loops L, aligning the holes of the conductive tape rings 2119 with corresponding holes in the middle part with double holes 2113, and adhered thereto. A second liner sheet is then removed from each of two conductive tape rings 2119 to reveal further bare adhesive faces thereof. Snap posts are emplaced through each of the wire loops L and corresponding holes in the garment G, and snaps are affixed thereto.

Figure 21L:
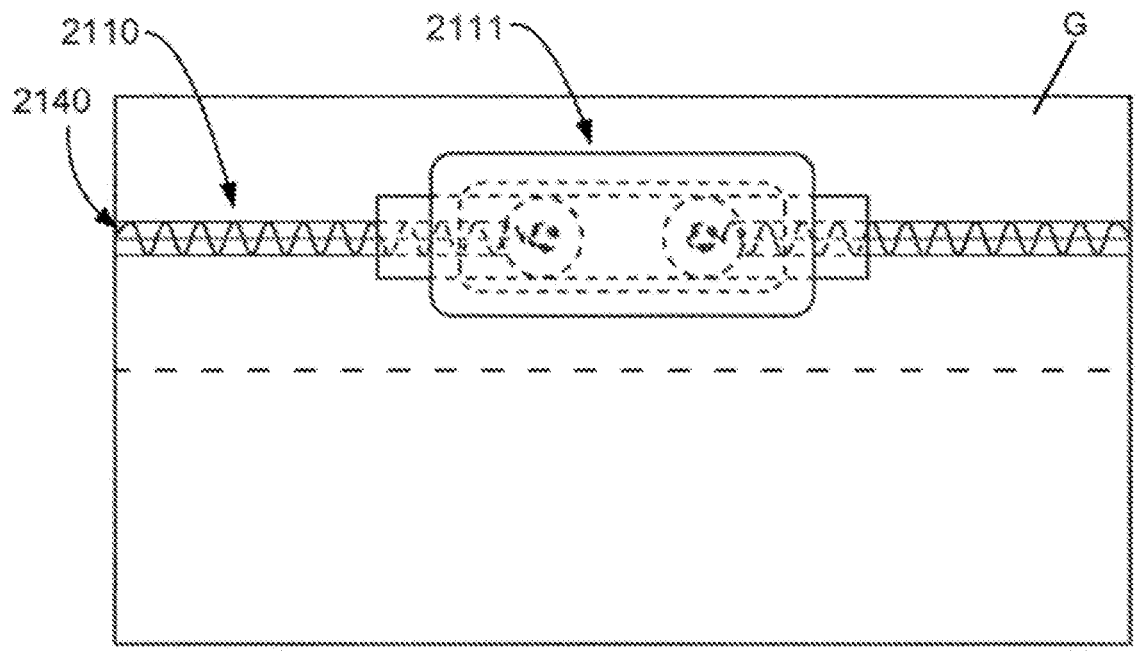
Figure 21M:
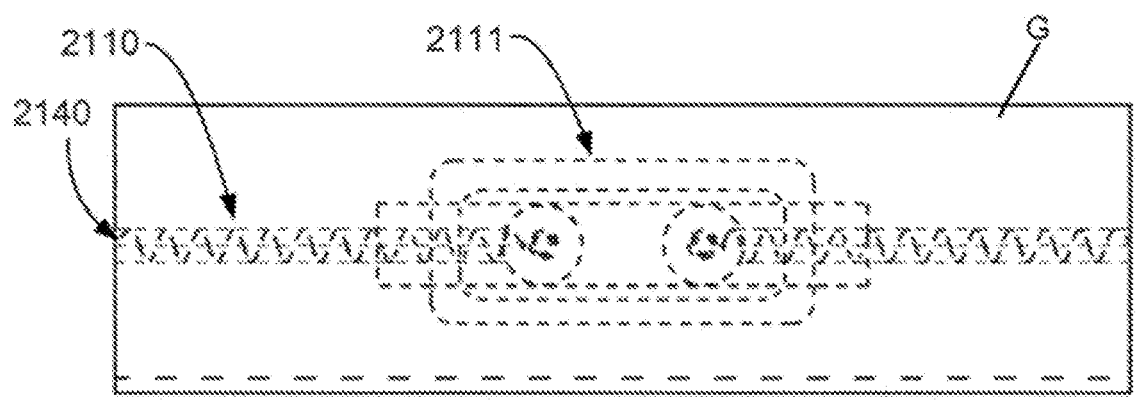

FIG. 21L shows garment G with the assembly and snaps in place, and a final cover 2125 covering the snaps (e.g., adhered in place by ironing, heat sealing, and/or the like). The garment G is then folded along a longitudinal fold line (see dashed line in FIGS. 21K and 21L), resulting in a folded band shown in FIG. 21M. In some embodiments, the folded band is stitched along at least one edge thereof.

Figure 22A:
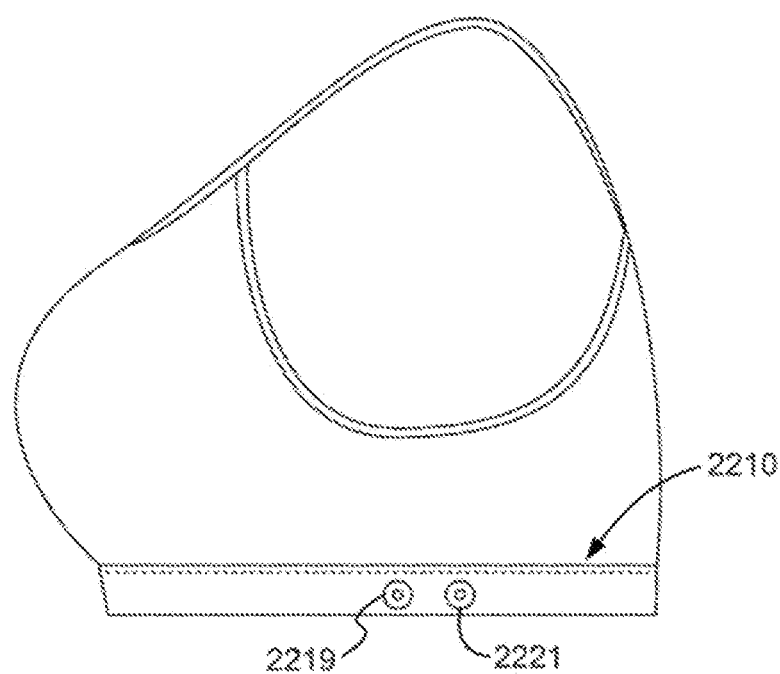
FIG. 22A shows an exterior view.
Figure 22B:
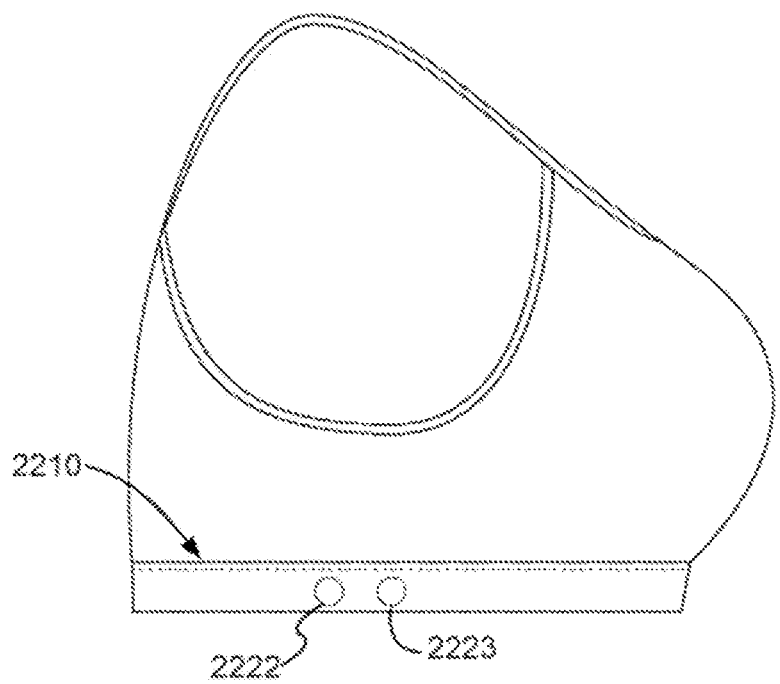
FIG. 22B shows an interior view, of an assembled biosensing garment, according to an embodiment.

FIG. 22A shows an exterior view, and 22B shows an interior view, of an assembled biosensing sports bra according to an embodiment. In FIG. 22A, two "sockets" 2219 and 2221 are visible along the lower hem of the sports bra, substantially near a side of the biosensing sports bra. In FIG. 22B an interior portion of the biosensing sports bra of FIG. 22A is shown, in which two "caps" 2222 and 2223 (of the connectors comprising the socket connectors of FIG. 22A) are visible and are covered by an inner layer of fabric of the biosensing sports bra.

Figure 23A:
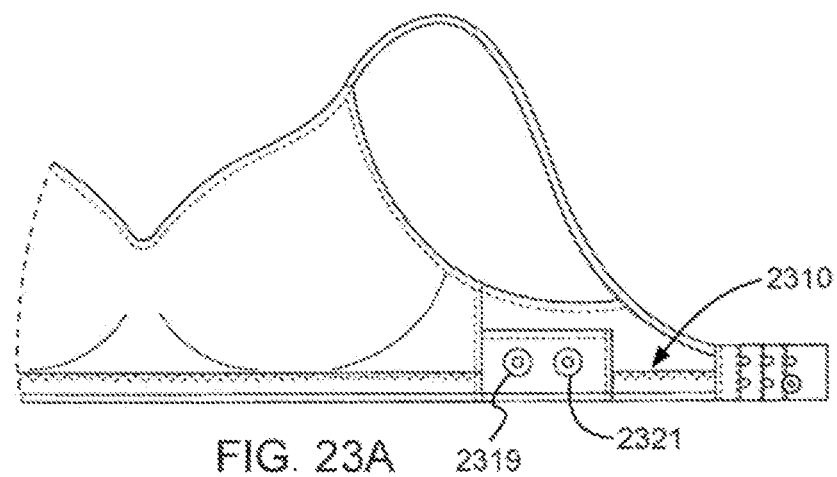
FIGS. 23A-23C show views of an assembled biosensing garment, according to an embodiment.
Figure 23B:
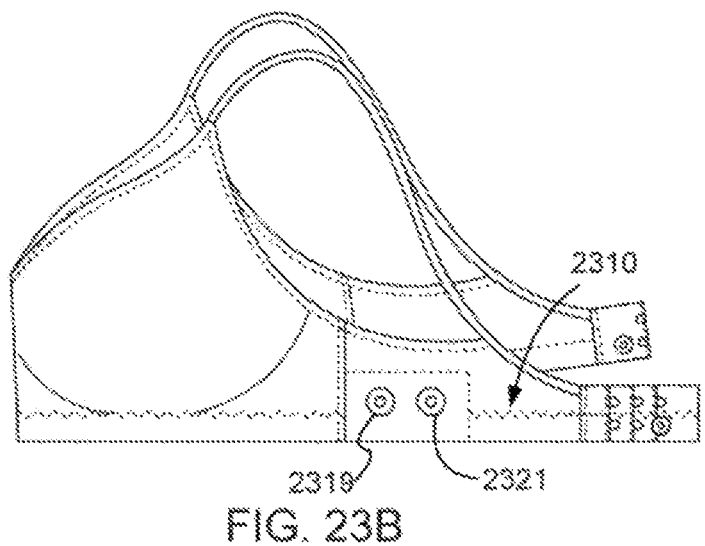
Figure 23C:
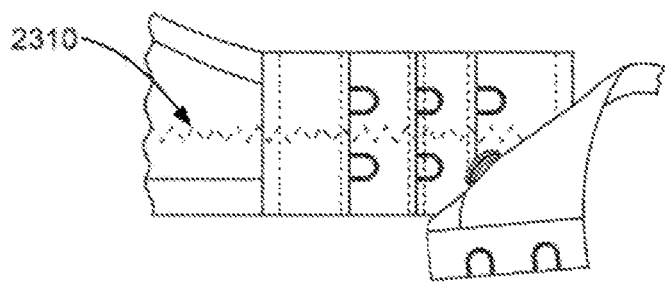

FIGS. 23A-23C show views of an assembled biosensing brassiere according to an embodiment. In FIG. 23A, two "sockets" 2319 and 2321 are visible near a lower band (e.g., an elastic material and/or a "soft" or "comfort material, etc.) of the biosensing brassiere, substantially near a left side (wearer's perspective) of the biosensing brassiere. FIG. 23B shows both an outer view of the left brassiere strap, including the sockets 2319 and 2321 of FIG. 23A as well as a modified "eye" portion of a traditional "hook and eye" closure. One of the six "eyes" of the hook and eye closure has been replaced with a "stud" that is connectable with a corresponding socket located on an inner surface of the right strap of the brassiere (also shown in FIG. 23B). FIG. 23C shows a close-up view of the connection made between the stud and the socket connectors of the brassiere of FIGS. 23A-23B. In some embodiments, the connection may instead be made by connecting stripped ends of the physiological sensor wires, on an inner surface of the biosensing brassiere, to multiple (e.g., 3) of the "hook" closure elements, thereby maintaining the adjustability of the brassier closure. Such connection can be made, for example, by stitching, crimping, twisting, applying conductive adhesive and/or laminating.

Figure 24A:
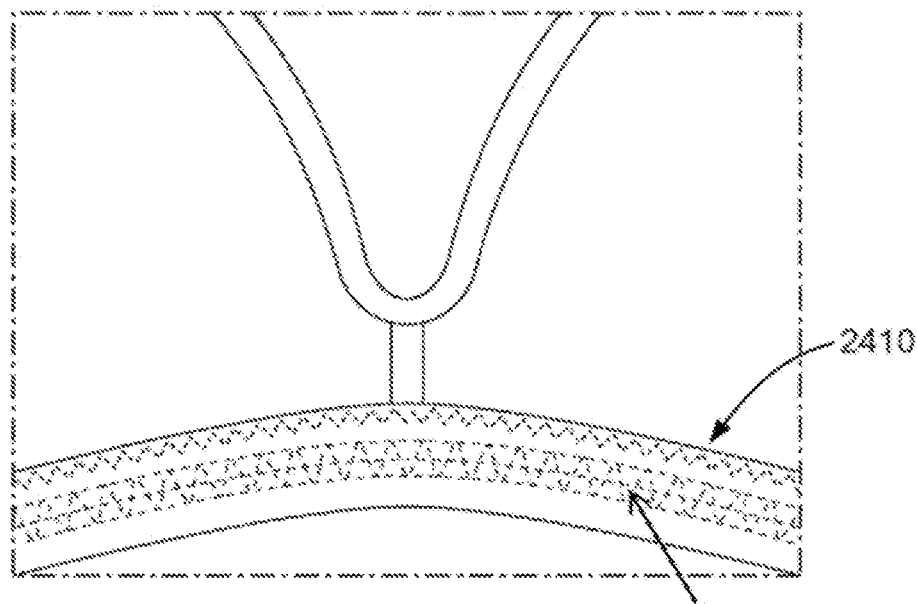
FIG. 24A shows an interior view.
Figure 24B:
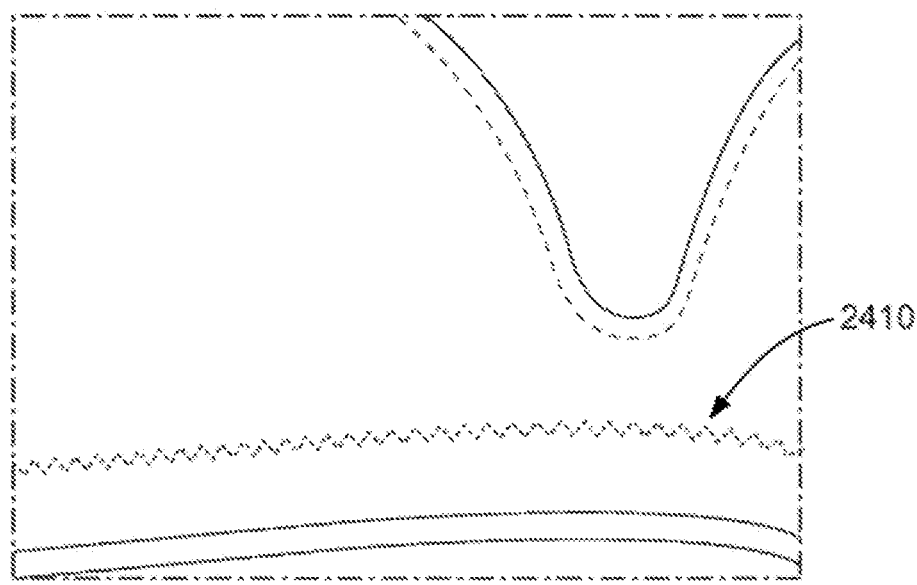
FIG. 24B shows an exterior view, of an assembled biosensing garment, according to an embodiment.

FIG. 24A shows an interior view of the lower band of the biosensing brassiere of FIGS. 23A-23C. As indicated by the arrow "A," the physiological sensor is positioned beneath an inner fabric layer of the lower band of the brassiere, and its contours are faintly visible through the inner fabric. The physiological sensor is thus disposed such that, when the straps of the biosensing brassiere are connected during use by a user, the physiological sensor (e.g., including an elongate member and conductive wire, as described herein) traverses the circumference of the user. FIG. 24B shows an exterior view of the biosensing brassiere of FIGS. 23A-23C and FIG. 24A, illustrating that the physiological sensor is not externally visible.

Figure 25A:
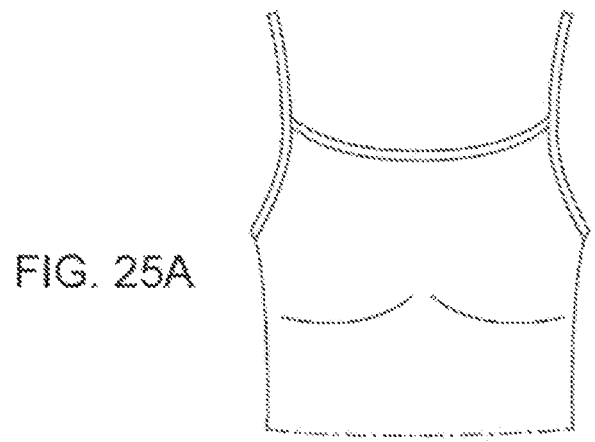
FIGS. 25A-25C show views of an assembled biosensing garment, according to an embodiment.
Figure 25B:
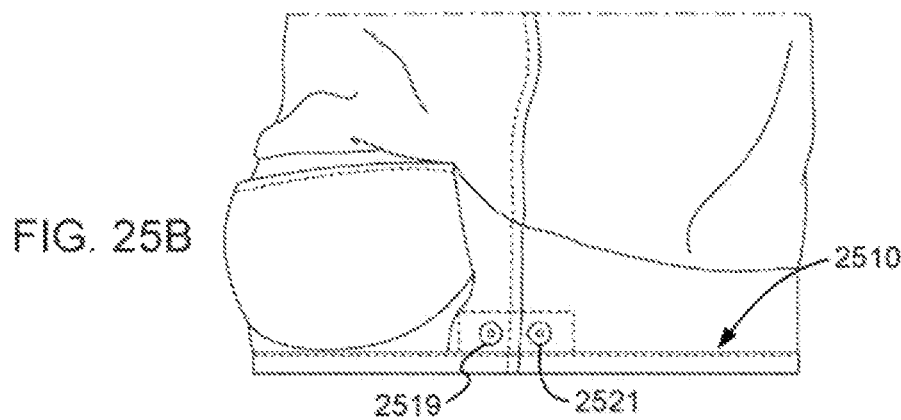
Figure 25C:
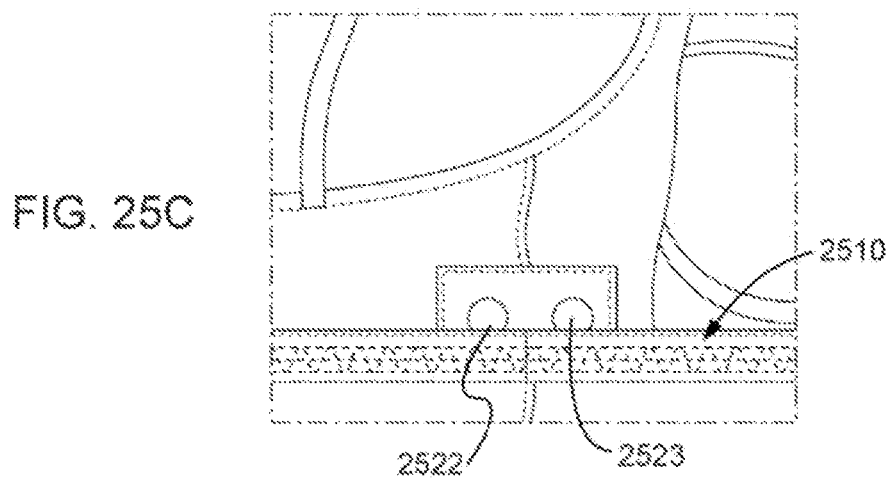

FIGS. 25A-25C show views of a biosensing bra cami (or "camisole brassiere") according to an embodiment. A bra cami is a camisole that has an integral brassiere connected to it (e.g., stitched to it, and in some instances sharing common shoulder straps). FIG. 25A shows an overall, exterior view of a biosensing bra, illustrating that the physiological sensor is not externally visible. FIG. 25B shows an interior view of the biosensing bra cami, including an exterior left side (wearer's perspective) view of the integral brassiere. In FIG. 25B, two "sockets" 2519 and 2521 are visible near a lower band of the integral brassiere. FIG. 25C shows an interior portion of the biosensing bra cami of FIG. 25A. Two "caps" 2522 and 2523 (of the connectors comprising the socket connectors of FIG. 25B) are visible and are covered by an inner layer of fabric of the biosensing bra cami.

In some embodiments, an apparatus according to the present disclosure includes an elongate member having a longitudinal axis and configured to be stretchable along its longitudinal axis. The elongate member includes a plurality of elastic members: a first elastic member, a second elastic member that extends substantially parallel to the first elastic member, and a third elastic member that extends substantially parallel to the second elastic member. A conductive member (or "wire") is coupled to the first, second and third members, and forms a "curved" pattern along the longitudinal axis of the elongate member. The conductive member (and, correspondingly, its curved pattern) is configured to change from a first configuration to a second configuration as the elongate member stretches along its longitudinal axis. This change of configuration results in a change in an inductance value of the conductive member. In some embodiments, instead of a curved pattern, the conductive member may be combined with the first, second and third elastic members such that it has a sawtooth, square, or triangle shape along at least a portion of its length. In some embodiments, multiple conductive members may be coupled to the elongate member, the conductive members having like or different patterns, or a single conductive member with a substantially constant pattern (i.e., shape and/or periodicity), or multiple conductive members each having a different pattern (i.e., shape and/or periodicity). The patterns of the conductive members described herein may be periodic, aperiodic, symmetric, and/or asymmetric along portions of or the entireties of their length(s). In some embodiments, the patterns of the conductive members described herein may be present along only portions of the elongate member, the rest of the elongate member (and/or the conductive member embedded therewithin) being substantially "straight."

In some embodiments, a method of making an elongate member involves forming a first elastic member, forming a second elastic member, forming a third elastic member, and braiding a conductive member (e.g., a wire having an insulating coating or shielding) with the first, second and third elastic members such that the conductive member has a curved (e.g., sinusoidal) pattern. In some embodiments, instead of a curved pattern, the conductive member may be combined with the first, second and third elastic members such that it has a sawtooth, square, or triangle shape along at least a portion of its length. In some embodiments, multiple conductive members may be coupled to the elongate member, the conductive members having like or different patterns, or a single conductive member with a substantially constant pattern (i.e., shape and/or periodicity), or multiple conductive members each having a different pattern (i.e., shape and/or periodicity). The patterns of the conductive members described herein may be periodic, aperiodic, symmetric, and/or asymmetric along portions of or the entireties of their length(s). In some embodiments, the patterns of the conductive members described herein may be present along only portions of the elongate member, the rest of the elongate member (and/or the conductive member embedded therewithin) being substantially "straight."

In some embodiments, a method of manufacturing a biosensing element includes knitting a first elastic member from a single yarn, forming at least one further elastic member, and threading a conductive wire through a filament of the single yarn and the at least one further elastic member. The conductive wire has a substantially fixed curved pattern and joins the single yarn and the at least one further elastic member to form an elongate member.

In some embodiments, an apparatus according to the present disclosure includes an elongate member having a longitudinal axis and configured to be stretchable along its longitudinal axis. The elongate member includes a plurality of substantially parallel elastic members and a conductive member comprising an electrical conductor. The conductive member is coupled to the elongate member by physical connection to at least one of the plurality of elastic members. The conductive member is disposed in a regular pattern along the longitudinal axis of the elongate member. The regular pattern corresponds to a first inductance value of the conductive member. The conductive member is configured to change from a first configuration to a second configuration in response to an applied force, the change from the first configuration to the second configuration resulting in a change from the first inductance value of the conductive member to a second inductance value of the conductive member.

As used herein, the terms "about" and "approximately" generally mean plus or minus 10% of the value stated, for example about 250 p.m would include 225 p.m to 275 p.m, about 1,000 p.m would include 900 p.m to 1,100 p.m.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. An apparatus comprising:
   an elongate member defining a longitudinal axis and configured to be stretchable along the longitudinal axis, the elongate member comprising one or more elastic members, at least one elastic member of the one or more elastic members comprising one or more strands of non-elastic multifilament and one or more strands of elastic filament that are twisted together; and
   a conductive member coupled to the one or more elastic members along the longitudinal axis of the elongate member, the conductive member being configured to change from a first configuration to a second configuration as the elongate member stretches along the longitudinal axis, the change from the first configuration to the second configuration resulting in a change of inductance of the conductive member.

2. The apparatus of claim 1, wherein the one or more elastic members comprises a first elastic member spaced a non-zero distance from a second elastic member and being substantially parallel.

3. The apparatus of claim 2, wherein the one or more elastic members further comprises a third elastic member that is substantially parallel to the first elastic member and the second elastic member, the third elastic member being spaced a non-zero distance from the second elastic member.

4. The apparatus of claim 3, wherein the elongate member is configured to be stretchable along the longitudinal axis in response to a force.

5. The apparatus of claim 4, wherein one or more of the first elastic member, second elastic member, and third elastic member are configured to change the conductive member from the second configuration back to the first configuration in response to a reduction or a removal of the force.

6. The apparatus of claim 1, wherein, each of the one or more stands of non-elastic multifilament is texturized.

7. The apparatus of claim 1, wherein the conductive member is coupled to the one or more elastic members in a curved pattern.

8. The apparatus of claim 7, wherein the curved pattern of the conductive member is substantially sinusoidal.

9. The apparatus of claim 1, wherein the conductive member is integrally formed with the elongate member in a curved pattern.

10. The apparatus of claim 9, wherein the conductive member is knitted with the one or more elastic members in the curved pattern.

11. The apparatus of claim 10, wherein the conductive member is weft knitted.

12. An apparatus comprising:
    an elongate member defining a longitudinal axis and configured to be stretchable along the longitudinal axis, the elongate member including a plurality of substantially parallel elastic members; and
    a conductive member comprising an electrical conductor, the conductive member fixedly coupled to at least one of the plurality of substantially parallel elastic members, the conductive member disposed along the longitudinal axis of the elongate member and configured to move between a first configuration and a second configuration, the conductive member having a first inductance value in the first configuration, and a second inductance value in the second configuration, wherein the plurality of elastic members are knitted from yarn, the yarn comprising one or more strands of non-elastic multifilament and one or more strands of elastic filament that are entwined or interwoven together.

13. The apparatus of claim 12, wherein the conductive member is disposed along the longitudinal axis of the elongate member in a curved pattern.

14. The apparatus of claim 13, wherein the curved pattern of the conductive member is substantially sinusoidal.

15. The apparatus of claim 12, further comprising: a first connector coupled to a first end of the elongate member and a second connector coupled to a second end of the elongate member, the first connector disposed proximate the second connector thereby forming an open loop.

16. The apparatus of claim 15, wherein the open loop is disposed in at least one of a substantially circular shape, a substantially oval shape, a substantially square shape, a substantially rectangular shape, and an irregularly shape.

17. The apparatus of claim 12, wherein the elongate member includes a first portion extending from a first connector in a first direction, and a second portion extending in a second direction from the first portion to a second connector, the second direction being opposite the first direction.

18. The apparatus of claim 17, wherein the second connector is proximate the first connector.

19. The apparatus of claim 17, wherein the second portion is folded back onto the first portion.

20. An apparatus comprising:
a plurality of substantially parallel elastic members disposed along an axis and configured to be stretchable along the axis; and
a conductive member disposed along the axis and fixedly coupled to at least one of the plurality of substantially parallel elastic members, the conductive member configured to move between a first configuration and a second configuration, the conductive member having a first inductance value in the first configuration, and a second inductance value in the second configuration, wherein the plurality of substantially parallel elastic members are knitted from woven yarn, the woven yarn comprising at least two strands of non-elastic multifilament and at least one strand of elastic filament.

* * * * *